United States Patent
Lee et al.

(10) Patent No.: US 10,221,433 B2
(45) Date of Patent: Mar. 5, 2019

(54) MICROORGANISMS HAVING PUTRESCINE PRODUCTIVITY AND PROCESS FOR PRODUCING PUTRESCINE USING THE SAME

(71) Applicant: CJ CHEILJEDANG CORPORATION, Seoul (KR)

(72) Inventors: Kyoung Min Lee, Seoul (KR); Hee Kyoung Jung, Seoul (KR); Young Lyeol Yang, Gyeonggi-do (KR); Hye Won Um, Gyeonggi-do (KR); Chang Gyeom Kim, Seoul (KR); Hong Xian Li, Seoul (KR); Su Jin Park, Seoul (KR); Jong Hyun Yoon, Gyeonggi-do (KR); Baek Seok Lee, Seoul (KR); Sun Young Lee, Daejeon (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 14/778,383

(22) PCT Filed: Feb. 25, 2014

(86) PCT No.: PCT/KR2014/001509
§ 371 (c)(1),
(2) Date: Sep. 18, 2015

(87) PCT Pub. No.: WO2014/148743
PCT Pub. Date: Sep. 25, 2014

(65) Prior Publication Data
US 2017/0002386 A1    Jan. 5, 2017

(30) Foreign Application Priority Data
Mar. 20, 2013 (KR) .................. 10-2013-0030020
Feb. 14, 2014 (KR) .................. 10-2014-0017243

(51) Int. Cl.
| C12N 1/15 | (2006.01) |
| C12N 1/21 | (2006.01) |
| C12P 13/00 | (2006.01) |
| C12N 9/02 | (2006.01) |
| C12N 9/10 | (2006.01) |
| C12N 9/12 | (2006.01) |
| C12N 9/88 | (2006.01) |
| C12N 15/52 | (2006.01) |

(52) U.S. Cl.
CPC .......... *C12P 13/001* (2013.01); *C12N 9/0008* (2013.01); *C12N 9/1018* (2013.01); *C12N 9/1029* (2013.01); *C12N 9/1096* (2013.01); *C12N 9/1217* (2013.01); *C12N 9/88* (2013.01); *C12N 15/52* (2013.01); *C12Y 102/01038* (2013.01); *C12Y 201/03003* (2013.01); *C12Y 203/01035* (2013.01); *C12Y 206/01011* (2013.01); *C12Y 207/02008* (2013.01); *C12Y 401/01007* (2013.01)

(58) Field of Classification Search
None
See application file for complete search history.

(56) References Cited

U.S. PATENT DOCUMENTS

| 7,332,310 | B2 | 2/2008 | Nakagawa et al. | |
| 9,290,771 | B2 * | 3/2016 | Lee ................. | C12N 15/77 |
| 2014/0004577 | A1 * | 1/2014 | Choi ................. | C07K 14/34 |
| | | | | 435/128 |

FOREIGN PATENT DOCUMENTS

| CN | 101679964 A | 3/2010 | |
| EP | 1849874 B1 | 5/2010 | |
| KR | 1020120064046 A | 6/2012 | |
| TW | 201441367 A | 11/2014 | |
| WO | WO 2012077995 A2 * | 6/2012 | ............ C07K 14/34 |
| WO | WO 2012/114256 A1 | 8/2012 | |
| WO | WO 2013105827 A2 * | 7/2013 | ........... C12N 9/1029 |

OTHER PUBLICATIONS

Morris et al., "Putrescine Biosynthesis in *Escherichia coli*", J. Biol. Chem. 244:6094-6099, 1969.*
Kind et al., Metabolic Engineer. 13:617-627, 2011.*
Nakamura et al., Appl. Environ. Biotechnol. 88:859-868, 2010.*
Hwang et al., J. Microbiol. Biotechnol. 18:704-710, 2008.*
Kind et al., Appl. Environ. Microbiol. 76:5175-5180, 2010.*
Zhou et al., "Global analysis of gene transcription regulation in prokaryotes", Cell Mol Life Sci 63:2260-2290, 2006 (Year: 2006).*
Kozak, M., "Initiation of translation in prokaryotes and eukaryotes", Gene 234:187-208, 1999 (Year: 1999).*
Nakagawa, S., "Permeases of the major facilitator superfamily [Corynebacterium glutamicum ATCC 13032]," Genbank Accession No. BAC00005, accessed Apr. 29, 2009.
Schneider et al., "Putrescine production by engineered Corynebacterium glutamicum," Appl Microbiol Biotechnol 88:859-868, 2010.
Zahoor et al., "Metabolic Engineering of Corynebacterium Glutamicum Aimed at Alternative Carbon Sources and New Products," Computational and Structural Biotechnology Journal 3(4):1-11, Oct. 2012.

* cited by examiner

*Primary Examiner* — David Steadman
(74) *Attorney, Agent, or Firm* — Cooley LLP

(57) ABSTRACT

The present invention relates to a recombinant microorganism capable of producing putrescine, in which the microorganism is modified to have enhanced NCgl2522 activity, thereby producing putrescine in a high yield, and a method for producing putrescine using the microorganism.

10 Claims, 1 Drawing Sheet
Specification includes a Sequence Listing.

[FIG. 1]
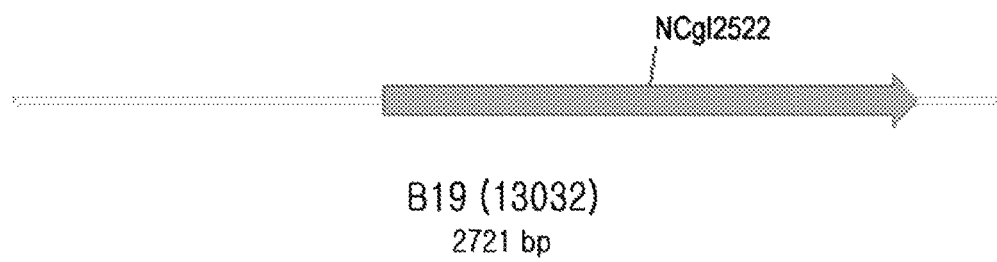
[FIG. 2]
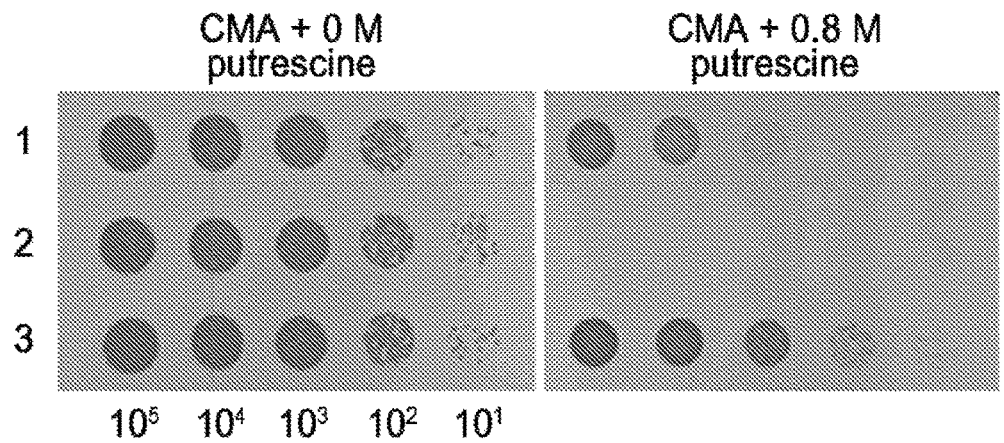

MICROORGANISMS HAVING PUTRESCINE PRODUCTIVITY AND PROCESS FOR PRODUCING PUTRESCINE USING THE SAME

CROSS-REFERENCES TO RELATED APPLICATIONS

This application is a U.S. national phase application of International PCT Patent Application No. PCT/KR2014/001509, which was filed on Feb. 25, 2014, which claims priority to Korean Patent Application Nos. 10-2014-0017243, filed Feb. 14, 2014 and 10-2013-0030020, filed Mar. 20, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_035_01US_ST25.txt. The text file is 48 KB, was created on Sep. 21, 2016, and is being submitted electronically via EFS-Web.

BACKGROUND OF THE INVENTION

1. Field of the Invention

The present invention relates to a recombinant microorganism having improved putrescine productivity and a method for producing putrescine at a high yield using the same.

2. Description of the Related Art

Polyamines such as spermidine, spermine or the like are present in most living cells, and putrescine (or 1,4-butanediamine) is used as a precursor in spermidine and spermine metabolisms. Putrescine is found in Gram-negative bacteria or fungus, and it is present in high concentrations in various species, suggesting that it has an important role in the metabolic pathways of microorganisms.

In general, putrescine is an important raw material in a synthesis of polyamine nylon-4, 6 which is produced by reacting with adipic acid. Putrescine is produced mainly by chemical synthesis through acrylonitrile and succinonitrile from propylene. This chemical synthesis is a three-step process including a catalytic oxidation reaction, a reaction using a cyanide compound, and a hydrogenation reaction using high-pressure hydrogen. There are problems in that this chemical synthesis is not environment friendly and also consumes a lot of energy leading to depletion of petroleum. Therefore, a more environment friendly and energy-effective method involving biomass utilization needs to be developed for putrescine production.

In microorganisms, a biosynthetic pathway of putrescine is the same as route of arginine synthesis from glutamate to ornithine synthesis. Putrescine can be biosynthesized through two pathways from microorganisms. In one pathway, ornithine as an intermediate is decarboxylated to synthesize putrescine. In the other pathway, agmatine is produced by decarboxylation arginine synthesized from ornithine, and then putrescine is synthesized from the agmatine (Morris et al., J Biol. Chem. 241: 13, 3129-3135, 1996). These two pathways produce the energy required for metabolism or allow the cell to have resistance to oxidative stress.

As a method for producing putrescine using a microorganism, a method for producing putrescine at a high concentration by transformation of *E. coli* and *Corynebacterium* has been reported (International Patent Publication No. WO06/005603; International Patent Publication No. WO09/125924; Qian ZD et al., Biotechnol. Bioeng. 104: 4, 651-662, 2009; Schneider et al., Appl. Microbiol. Biotechnol. 88: 4, 859-868, 2010; Schneider et al., Appl. Microbiol. Biotechnol. 91: 17-30, 2011). For example, WO09/125924 discloses a method for producing putrescine in a high yield by enhancing ornithine biosynthetic pathway, instead of inactivating pathways involved in degradation and utilization of putrescine which are present in *E. coli* and inactivating conversion of ornithine as a precursor of putrescine to arginine. In addition, Schneider (2010) discloses a method for producing putrescine at a high concentration by introducing and enhancing a protein capable of converting ornithine to putrescine into a *Corynebacterium* sp. strain having no putrescine productivity.

Furthermore, studies on putrescine transporters in *E. coli*, yeast, plant and animal cells have been actively conducted (K Igarashi, Plant Physiol. Biochem. 48: 506-512, 2010). Putrescine uptake of *E. coli* occurs via 4 pathways; potA-BCD or potFGHI driven by ATP hydrolysis, andpotE as H+ symporter and puuP of the puu pathway. With regard to Km values of these complexes involved in putrescine uptake, those of PotFGHI, potABCD, potE and puuP are 0.5 mM, 1.5 mM, 1.8 mM, and 3.7 mM, respectively. Among the four putrescine uptake pathways, potFGHI complex is considered as the most suitable. In addition, potE transporter has both functions of uptake and excretion of putrescine. Putrescine is imported together with proton into cells at neural pH. However, as putrescine synthase (speF) is expressed under acidic pH conditions, intracellular uptake of extracellular ornithine and extracellular excretion of putrescine synthesized within cells occur at the same time (Kurihara et. al., J. Bacteriology 191: 8, 2776-2782, 2009).

The known putrescine exporters in yeast are TPO1 and TPO4. These amino acid sequence are very similar to the amino acid sequence of *bacillus* multidrug transporter Blt. These two exporters share characteristics with potE in *E. coli*, and they have functions of importing putrescine, spermidine, and spermine under basic conditions and exporting them under acidic conditions. In addition, yeast cell overexpressing TPO5 gene is resistant to 120 mM putrescine whereas a mutant disrupted TPO5 gene is sensitive to 90 mM putrescine (Tachihara et. al., J. Biological Chemistry, 280(13): 12637-12642, 2005).

Synthesis and degradation, and uptake and excretion of putrescine in animal cells are regulated in various ways. Although studies on polyamine excretion have not been done in animal cells as well as in *E. coli* or yeast, there is a report that an SLC3A2 (arginine/diamine exporter) functions to import arginine into cells and to export putrescine, acetyl spermidine, and acetyl spermine in colon epithelial cells. However, there has been no report about uptake and export of putrescine in plant cells (Igarashi et al., Plant Physiol. & Biochem. 48: 506-512, 2010).

On the other hand, since *Corynebacterium* sp. microorganism has no putrescine biosynthetic pathway, studies regarding putrescine export have not been studied. According to a recent report, cell growth is restored and cadaverine productivity is increased by overexpression of a cg2983 membrane protein in a strain producing a cadaverine (Kind et. al., Metabolic Engineering 13: 617-627, 2011).

However, there have been no reports about association between putrescine exporter and putrescine productivity or growth of microorganisms producing putrescine. In the above literature, there is no mention about association between cg2983 membrane protein and the exporting ability of putrescine.

In this background, the present inventors have made many efforts to develop a strain capable of producing putrescine in a higher yield. As a result, NCgl2522 functions is revealed as a putrescine exporter in a putrescine-producing strain, *Corynebacterium* sp. microorganism, and putrescine can be produced in a high yield by enhancing NCgl2522 activity, compared to the endogenous activity thereof. In addition, the amount of putrescine in a culture medium can be increased by expressing NCgl2522 in *E. coli* having the putrescine synthetic pathway, and thus the present inventors suggested that NCgl2522 also functions as a putrescine exporter in *E. coli*, thereby completing the present invention.

SUMMARY OF THE INVENTION

An object of the present invention is to provide a recombinant microorganism which is modified to have enhanced NCgl2522 activity, thereby produced putrescine in a high yield.

Another object of the present invention is to provide a method for producing putrescine in a high yield using the microorganism.

BRIEF DESCRIPTION OF THE DRAWINGS

FIG. 1 is a diagram showing that NCgl2522 is included in a clone (B19) finally selected from the transformed colonies introduced with *Corynebacterium* chromosome library according to the present invention; and FIG. 2 is the result of evaluating putrescine resistance of the NCgl2522-deleted or -enhanced recombinant strain according to the present invention.
  1: KCCM11240P
  2: KCCM11240P ΔNCgl2522
  3: KCCM11240P P(CJ7)-NCgl2522

DETAILED DESCRIPTION OF THE PREFERRED EMBODIMENTS

In one aspect to achieve the above object, the present invention provides a microorganism having putrescine productivity, which is modified to enhance activity of a protein having an amino acid sequence represented by SEQ ID NO: 21 or 23.

In one specific embodiment, the present invention provides a microorganism having putrescine productivity, in which the microorganism is further modified to have weakened activities of ornithine carbamoyltransferase (ArgF) and a protein (NCgl1221) involved in glutamate export, compared to the endogenous activities thereof, and is introduced with ornithine decarboxylase (ODC) activity.

In another specific embodiment, the present invention provides a microorganism having putrescine productivity, in which the ornithine carbamoyltransferase (ArgF) has an amino acid sequence represented by SEQ ID NO: 29, the protein (NCgl1221) involved in glutamate export has an amino acid sequence represented by SEQ ID NO: 30, and the ornithine decarboxylase (ODC) has an amino acid sequence represented by SEQ ID NO: 33.

In still another specific embodiment, the present invention provides a microorganism having putrescine productivity, in which the microorganism is further modified to have enhanced activities of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD), compared to the endogenous activities thereof.

In still another specific embodiment, the present invention provides a microorganism having putrescine productivity, in which the acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) have amino acid sequences represented by SEQ ID NOs: 25, 26, 27 and 28, respectively.

In still another specific embodiment, the present invention provides a microorganism having putrescine productivity, in which acetyltransferase (NCgl1469) activity of the microorganism is further weakened.

In still another specific embodiment, the present invention provides a microorganism having putrescine productivity, in which the acetyltransferase has an amino acid sequence represented by SEQ ID NO: 31 or 32.

In still another specific embodiment, the present invention provides a microorganism having putrescine productivity, in which the microorganism is an *Escherichia* sp. or a *Corynebacterium* sp.

In still another specific embodiment, the present invention provides a microorganism having putrescine productivity, in which the microorganism is *E. coli* or *Corynebacterium glutamicum*.

In another aspect, the present invention provides a method for producing putrescine, comprising the steps of culturing a microorganism having putrescine productivity to obtain a cell culture and recovering putrescine from the cultured microorganism or cell culture.

Hereinafter, the present invention will be described in detail.

The present invention provides a recombinant *Corynebacterium* sp. microorganism, in which the *Corynebacterium* sp. microorganism having putrescine productivity is modified to have enhanced NCgl2522 activity, compared to the endogenous activity thereof and thus it has improved putrescine productivity.

As used herein, the term "NCgl2522" refers to permease belonging to MFS (major facilitator superfamily), which is a membrane protein isolated from *Corynebacterium glutamicum* ATCC13032. NCgl2522 is known to export diaminopentane from *Corynebacterium glutamicum*. In the present invention, NCgl2522 was confirmed to function as a transporter that serves to extracellularly export putrescine produced within cells. On the basis of this fact, the present invention provides a recombinant microorganism showing high-yield putrescine productivity, in which NCgl2522 is modified to have enhanced activity, compared to the endogenous activity thereof, and therefore, export of intracellularly produced putrescine is increased.

As used herein, the term "endogenous activity" refers to the activity of an enzyme that a microorganism possesses in its native state, namely in the state without modification, and the meaning of "modified to have enhanced activity, compared to the endogenous activity" is that the activity of the enzyme is newly introduced or further improved, compared to the activity of the corresponding enzyme before modification.

In the present invention, "enhancement of enzymatic activity" includes improvement in the enzymatic activity by improvement in endogenous gene activity, amplification of the endogenous gene by internal or external factors, deletion of a regulatory factor for suppressing the gene expression, increase in the gene copy number, increase in the activity by introduction of a foreign gene or modification of an expression regulatory sequence, in particular, replacement or modification of a promoter and mutation within gene, as well as introduction or improvement of the activity of the enzyme itself to achieve effects beyond the endogenous functions.

In the present invention, "modified to have enhanced activity, compared to the endogenous activity" means that the activity of the microorganism is increased after manipulation such as introduction of a gene showing the activity, or increase in the gene copy number, deletion of a regulatory factor for suppressing the gene expression or modification of an expression regulatory sequence, for example, use of an improved promoter, compared to the activity of the microorganism before the manipulation.

The NCgl2522, having its activity is increased by the present invention, may be, but is not particularly limited to, a protein having an amino acid sequence of SEQ ID NO: 21 or 23 or an amino acid sequence having 70% or more homology thereto, preferably 80% or more homology thereto, more preferably 90% or more homology thereto, much more preferably 95% or more homology thereto, much more preferably 98% or more homology thereto, and most preferably 99% or more homology thereto. Further, because the amino acid sequence of the protein showing the activity may differ depending on species or strain of the microorganism, the protein is not limited thereto. That is, the protein may be a protein mutant or an artificial variant that has an amino acid sequence including substitution, deletion, insertion, or addition of one or several amino acids at one or more positions of the amino acid sequence of SEQ ID NO: 21 or 23, as long as the protein aids to improve putrescine productivity by enhancing its activity. As used herein, the term "several" amino acids means specifically 2 to 20, preferably 2 to 10, and more preferably 2 to 5 amino acids, although it may differ depending on the position or type of amino acid residue in the three-dimensional structure of the protein. Furthermore, the substitution, deletion, insertion, addition or inversion of amino acids may include naturally occurring mutations which occur due to differences of individual or species of the microorganism having the activity of the polypeptide or artificial variation.

There are no putrescine biosynthetic pathways in *Corynebacterium* sp. microorganism. However, when external ornithine decarboxylase (ODC) is introduced, putrescine is synthesized and excreted extracellularly, indicating presence of a transporter, that is, an exporter that functions as a passage of putrescine among numerous membrane proteins of *Corynebacterium* sp. microorganism. Accordingly, in order to isolate the putrescine exporter in *Corynebacterium* sp. microorganism, the present inventors prepared a chromosome library of the wild-type *Corynebacterium glutamicum* ATCC13032, and they transformed a putrescine-producing strain, *Corynebacterium glutamicum* KCCM11138P with the library, and selected strains that grow in a minimal medium containing putrescine. Through tertiary colony selection, a clone (B19) having putrescine resistance was finally selected and base sequence analysis was performed to confirm that the clone contains NCgl2522 (see FIG. 1). As the putrescine exporter, NCgl2522 derived from *Corynebacterium glutamicum* ATCC13032 has the amino acid sequence represented by SEQ ID NO: 21, and NCgl2522 derived from *Corynebacterium glutamicum* ATCC13869 which has 98% homology to the above amino acid sequence has the amino acid sequence represented by SEQ ID NO: 23.

A polynucleotide encoding NCgl2522 of the present invention may include a polynucleotide encoding the protein having the amino acid sequence of SEQ ID NO: 21 or 23, or the amino acid sequence having 70% or more homology thereto, preferably 80% or more homology thereto, more preferably 90% or more homology thereto, much more preferably 95% or more homology thereto, much more preferably 98% or more homology thereto, and most preferably 99% or more homology thereto, as long as the protein has the activity similar to that of the NCgl2522 protein, and most preferably, it may include a nucleotide sequence of SEQ ID NO: 20 or 22.

As used herein, the term "homology" refers to the similarity between two amino acid sequences, and can be determined using the well-known methods using BLAST 2.0, which calculates parameters such as score, identity, and similarity.

Further, the polynucleotide encoding NCgl2522 of the present invention may be a variant which hybridizes under stringent conditions with the nucleotide sequence of SEQ ID NO: 20 or 22, or a probe derived from the above nucleotide sequence, provided that it encodes a functional NCgl2522. As used herein, the term "stringent conditions" mean conditions allowing a specific hybridization between polynucleotides. For example, such stringent conditions are described in detail in the literature (J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

In the present invention, "modified to have enhanced NCgl2522 activity, compared to the endogenous activity" may be performed by a method selected from methods of increasing the copy number of the polynucleotide encoding the protein, modifying an expression regulatory sequence to increase expression of the polynucleotide, modifying the polynucleotide sequence on the chromosome to enhance the activity of the enzyme, deleting a regulatory factor for suppressing the gene expression, and combinations thereof.

The copy number of the polynucleotide may be, but is not particularly limited to, increased by operably linking the polynucleotide to a vector or by integrating it into the host cell genome. Specifically, the copy number of the polynucleotide in the host cell genome can be increased by introducing into the host cell the vector which is operably linked to the polynucleotide encoding the protein of the present invention and replicates and functions independently of the host cell, or by introducing into the host cell the vector which is operably linked to the polynucleotide and is able to integrate the polynucleotide into the host cell genome.

As used herein, the term "vector" refers to a DNA construct including a nucleotide sequence encoding the desired protein, which is operably linked to an appropriate expression regulatory sequence to express the desired protein in a suitable host cell. The regulatory sequence includes a promoter that can initiate transcription, an optional operator sequence for regulating the transcription, a sequence encoding a suitable mRNA ribosome binding site, and a sequence regulating the termination of transcription and translation. After the vector is transformed into the suitable host cell, it can replicate or function independently of the host genome, and can be integrated into the genome itself.

The vector used in the present invention is not particularly limited, as long as it is able to replicate in the host cell, and any vector known in the art can be used. Examples of conventional vectors may include a natural or recombinant plasmid, cosmid, virus and bacteriophage. For instance, pWE15, M13, MBL3, MBL4, IXII, ASHII, APII, t10, t11, Charon4A, and Charon21A may be used as a phage vector or cosmid vector. As a plasmid vector, pBR type, pUC type, pBluescriptII type, pGEM type, pTZ type, pCL type and pET type may be used. A vector usable in the present invention is not particularly limited, and any known expression vector can be used. Preferably, pDZ, pACYC177, pACYC184, pCL, pECCG117, pUC19, pBR322, pMW118, or pCC1BAC vector may be used, and more preferably, pDZ vector may be used.

Further, the polynucleotide encoding the desired protein in the chromosome can be replaced by a mutated polynucleotide using a vector for chromosomal insertion. The insertion of the polynucleotide into the chromosome may be performed by any method known in the art, for example, homologous recombination. Since the vector of the present invention can be inserted into the chromosome by homologous recombination, it may further include a selection marker to confirm chromosomal insertion. The selection marker is to select cells transformed with the vector, that is, to confirm insertion of the desired polynucleotide, and the selection marker may include markers providing selectable phenotypes, such as drug resistance, auxotrophy, resistance to cytotoxic agents, or surface protein expression. Only cells expressing the selection marker are able to survive or to show different phenotypes under the environment treated with the selective agent, and thus the transformed cells can be selected.

As used herein, the term "transformation" means the introduction of a vector including a polynucleotide encoding a target protein into a host cell in such a way that the protein encoded by the polynucleotide is expressed in the host cell. As long as the transformed polynucleotide can be expressed in the host cell, it can be either integrated into or placed in the chromosome of the host cell, or exist extrachromosomally. Further, the polynucleotide includes DNA and RNA encoding the target protein. The polynucleotide can be introduced in any form, as long as it can be introduced into the host cell and expressed therein. For example, the polynucleotide can be introduced into the host cell in the form of an expression cassette, which is a gene construct including all elements required for its autonomous expression. Typically, the expression cassette includes a promoter operably linked to the polynucleotide, transcriptional termination signals, ribosome binding sites, or translation termination signals. The expression cassette may be in the form of a self-replicable expression vector. Also, the polynucleotide as it is may be introduced into the host cell and operably linked to sequences required for expression in the host cell.

Further, as used herein, the term "operably linked" means a functional linkage between a polynucleotide sequence encoding the desired protein and a promoter sequence which initiates and mediates transcription of the polynucleotide sequence.

As well, modification of the expression regulatory sequence for increasing the polynucleotide expression may be, but is not limited to, done by inducing a modification on the expression regulatory sequence through deletion, insertion, non-conservative or conservative substitution of nucleotide sequence, or a combination thereof in order to further enhance the activity of expression regulatory sequence, or by replacing the expression regulatory sequence with a nucleotide sequence having stronger activity. The expression regulatory sequence includes, but is not particularly limited to, a promoter, an operator sequence, a sequence coding for ribosome-binding site, and a sequence regulating the termination of transcription and translation.

A strong heterologous promoter instead of the original promoter may be linked upstream of the polynucleotide expression unit, and examples of the strong promoter may include CJ7 promoter, lysCP1 promoter, EF-Tu promoter, groEL promoter, aceA or aceB promoter, and more preferably, lysCP1 promoter or CJ7 promoter as a *Corynebacterium*-derived promoter, and the polynucleotide encoding the enzyme is operably linked thereto so that its expression rate can be increased. Herein, the lysCP1 promoter is a promoter improved through nucleotide sequence substitution of the promoter region of the polynucleotide encoding aspartate kinase and aspartate semialdehyde dehydrogenase, and is a strong promoter that increases expression of the aspartate kinase gene, leading to 5-fold increased activity of the corresponding enzyme, compared to the wild-type (WO 2009/096689). Further, CJ7 promoter is a promoter that was found during exploration of a strong promoter sequence in *Corynebacterium ammoniagenes* and confirmed to be expressed in *Corynebacterium ammoniagenes* and *Escherichia* and to have a strong promoter activity. CJ7 promoter is a promoter that also shows high expression activity in *Corynebacterium glutamicum* (Korean Patent No. 0620092 and WO 2006/065095).

Furthermore, modification of a polynucleotide sequence on chromosome may be, but is not particularly limited to, done by inducing a mutation on the expression regulatory sequence through deletion, insertion, non-conservative or conservative substitution of polynucleotide sequence, or a combination thereof in order to further enhance the activity of the polynucleotide sequence, or by replacing the sequence with a polynucleotide sequence which is modified to have stronger activity.

In one preferred embodiment of the present invention, in order to provide a *Corynebacterium* sp. microorganism having improved putrescine productivity, the copy number of the gene can be increased by introducing into the chromosome the polynucleotide having the nucleotide sequence of SEQ ID NO: 20 or 22 encoding NCgl2522 involved in putrescine excretion, or the own promoter of NCgl2522 can be substituted with a promoter having improved activity, preferably, CJ7 promoter having the nucleotide sequence of SEQ ID NO: 24.

As used herein, the term "microorganism having putrescine productivity" or "microorganism producing putrescine" refers to a microorganism that is prepared by providing putrescine productivity for the parent strain having no putrescine productivity. The microorganism that is provided with putrescine productivity or produces putrescine may be, but is not particularly limited to, a microorganism having improved productivity of ornithine to be used as a raw material for putrescine biosynthesis, in which the microorganism is modified to have higher activities of acetylglutamate synthase converting glutamate to acetylglutamate (Nacetylglutamate) or ornithine acetyltransferase (ArgJ) converting acetyl ornithine to ornithine, acetylglutamate kinase (ArgB) converting acetyl glutamate to acetylglutamyl phosphate (N-acetylglutamyl phosphate), acetyl-gamma-glutamyl phosphate reductase (ArgC) converting acetyl glutamyl phosphate to acetyl glutamate semialdehyde (N-acetyl glutamate semialdehyde), or acetylornithine aminotransferase (ArgD) converting acetyl glutamate semialdehyde to acetylornithine (N-acetylornithine) than the endogenous activity, in order to enhance the biosynthetic pathway from glutamate to ornithine. Further, the microorganism is a microorganism that is modified to have weaker activity of ornithine carbamoyltransferase (ArgF) involved in synthesis of arginine from ornithine, the protein (NCgl1221) involved in glutamate excretion, and/or the protein (NCgl469) acetylating putrescine than the endogenous activity, and/or modified to have ornithine decarboxylase (ODC) activity.

In this regard, acetyl-gamma-glutamyl-phosphate reductase (ArgC), acetylglutamate synthase or ornithineacetyltransferase (ArgJ), acetylglutamate kinase (ArgB), acetylornithine aminotransferase (ArgD), ornithine carbamoyl transferase (ArgF), the protein (NCgl1221) involved in glutamate export, and ornithine decarboxylase (ODC) may have, but are not particularly limited to, preferably the amino acid sequences represented by SEQ ID NOs: 25, 26, 27, 28, 29, 30 and 33, respectively, or amino acid sequences having 70% or more homology thereto, more preferably 80% or more homology thereto, or much more preferably 90% or more homology thereto, respectively. In addition, the protein (NCgl469) acetylating putrescine may have, but is not particularly limited to, preferably the amino acid sequence represented by SEQ ID NO: 31 or 32, or an amino acid sequence having 70% or more homology thereto, more preferably 80% or more homology thereto, or much more preferably 90% or more homology thereto.

Of the proteins, the increase in the activities of acetyl-gamma-glutamyl-phosphate reductase (ArgC), acetylglutamate synthase or ornithineacetyltransferase (ArgJ), acetylglutamate kinase (ArgB), acetylornithine aminotransferase (ArgD), and ornithine decarboxylase (ODC) may be achieved by the above described method of increasing the NCgl2522 activity, for example, a method selected from the methods of increasing the copy number of the polynucleotide encoding the protein, modifying an expression regulatory sequence to increase expression of the polynucleotide, modifying the polynucleotide sequence on the chromosome to enhance the activity of the enzyme, deleting a regulatory factor to suppress the expression of the polynucleotide of the enzyme, and combinations thereof.

Further, activities of ornithine carbamoyl transferase (ArgF), the protein (NCgl1221) involved in glutamate export, and the protein (NCgl469) acetylating putrescine can be diminished by a method selected from the group consisting of a partial or full deletion of a polynucleotide encoding the protein, modification of an expression regulatory sequence for suppressing the polynucleotide expression, modification of the polynucleotide sequence on chromosome for diminishing the protein activity, and a combination thereof.

In detail, a partial or full deletion of the polynucleotide encoding the protein can be done by introducing a vector for chromosomal insertion into a microorganism, thereby substituting the polynucleotide encoding an endogenous target protein on chromosome with a partially removed polynucleotide or a marker gene. The "partial" may vary depending on the type of polynucleotide, but specifically refers to 1 to 300, preferably 1 to 100, and more preferably 1 to 50 nucleotides.

Also, modification of the expression regulatory sequence can be done by inducing a modification on the expression regulatory sequence through deletion, insertion, non-conservative or conservative substitution of nucleotide sequence, or a combination thereof in order to diminish the activity of expression regulatory sequence, or by replacing the expression regulatory sequence with a nucleotide sequence having weaker activity. The expression regulatory sequence includes a promoter, an operator sequence, a sequence coding for ribosome-binding site, and a sequence regulating the termination of transcription and translation.

Furthermore, modification of a polynucleotide sequence on chromosome can be done by inducing a mutation on the sequence through deletion, insertion, non-conservative or conservative substitution of polynucleotide sequence, or a combination thereof in order to further diminish the enzymatic activity, or by replacing the sequence with a polynucleotide sequence which is modified to have weaker activity.

Moreover, a regulatory factor for suppressing the expression of the polynucleotide of the enzyme can be deleted by substituting a polynucleotide of the expression suppressing factor with a partially removed polynucleotide or a marker gene. The "partial" may vary depending on the type of polynucleotide, but specifically refers to 1 to 300, preferably 1 to 100, and more preferably 1 to 50 nucleotides.

Meanwhile, the microorganism of the present invention is a microorganism having putrescine productivity, and includes a prokaryotic microorganism expressing the protein having the amino acid sequence represented by SEQ ID NO: 21 or 23, and examples thereof may include microorganisms belonging to *Escherichia* sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Selenomanas* sp., *Vibrio* sp., *Pseudomonas* sp., *Streptomyces* sp., *Arcanobacterium* sp., *Alcaligenes* sp. or the like. The microorganism of the present invention is preferably a microorganism belonging to *Escherichia* sp. or a microorganism belonging to *Corynebacterium* sp., and more preferably, *E. coli* or *Corynebacterium glutamicum*.

In a specific embodiment of the present invention, a *Corynebacterium* sp. microorganism with Accession No. KCCM11138P (Korean Patent Publication NO. 2012-0064046) and a *Corynebacterium* sp. microorganism with Accession No. KCCM11240P (Korean Patent Application NO. 2012-0003634) were used as strains that have enhanced synthetic pathway from glutamate to putrescine, thereby producing putrescine at a high concentration.

In still another embodiment of the present invention, *Corynebacterium glutamicum* ATCC13032-based putrescine-producing strains, KCCM11138P and KCCM11240P, and *Corynebacterium glutamicum* ATCC13869-based putrescine-producing strains DAB12-a and DAB12-b having the same genotype were used. ATCC13869 strain can be obtained from American Type Culture Collection (ATCC). That is, a unique accession number is listed in the catalog of ATCC is given for each strain, and the strain can be ordered using the accession number. Specifically, the putrescine-producing strain DAB12-a is characterized by deletion of a gene encoding ornithine carbamoyl transferase (ArgF) and a gene encoding the glutamate exporter NCgl1221, introduction of a gene encoding ornithine decarboxylase (OCD), and replacement of the promoter of ornithine biosynthetic gene operon (argCJBD) by an improved promoter in the *Corynebacterium glutamicum* ATCC13869. Further, the putrescine-producing strain DAB12-b is characterized in that it is prepared by modifying the DAB12-a strain to have weakened activity of the protein (NCgl1469) acetylating putrescine, compared to the endogenous activity.

According to one preferred Example, *Corynebacterium glutamicum* KCCM11138P prepared by deletion of the gene encoding ornithine carbamoyl transferase (ArgF) and a gene encoding the glutamate exporter NCgl1221, replacement of the own promoter of ArgCJBD gene cluster encoding an enzyme involved in the synthesis of ornithine from glutamate by an improved promoter, and introduction of the gene encoding ornithine decarboxylase (ODC) into the chromosome in the wild-type *Corynebacterium glutamicum* ATCC13032, and *Corynebacterium glutamicum* KCCM11240P prepared by additionally weakening a gene encoding the acetyltransferase NCgl1469 in the microorganism were prepared as putrescine-producing strains.

Meanwhile, in order to prepare an NCgl2522-deleted strain derived from *Corynebacterium glutamicum* ATCC13032, a plasmid pDZ-1'NCgl2522(K/O) was prepared, based on the nucleotide sequence of NCgl2522 derived from *Corynebacterium glutamicum* ATCC13032.

The plasmid pDZ-1'NCgl2522(K/O) was transformed into the prepared putrescine-producing strains, KCCM11138P and KCCM11240P, and selected as NCgl2522-deleted strains, and these strains were designated as KCCM11138P ΔNCgl2522 and KCCM11240P ΔNCgl2522, respectively. In the same manner, NCgl2522-deleted strains derived from *Corynebacterium glutamicum* ATCC13869 were prepared and designated as DAB12-a ΔNCgl2522 and DAB12-b ΔNCgl2522.

Putrescine productivities of 4 types of NCgl2522-deleted strains thus prepared were compared with that of the parent strain, and as a result, putrescine productivity was reduced in all of NCgl2522-deleted KCCM11138P ΔNCgl2522, KCCM11240P Δ NCgl2522, DAB12-a Δ NCgl2522, and DAB12-b Δ NCgl2522, compared to the parent strain (see Table 3). Based on this result, the present inventors confirmed that NCgl2522 activity in the putrescine-producing strain is closely related to putrescine productivity, and they prepared NCgl2522-enhanced strains in order to increase putrescine productivity through enhancement of the activity.

To this end, in one preferred Example of the present invention, NCgl2522 was additionally introduced into the transposon of *Corynebacterium glutamicum* strain or the own NCgl2522 promoter within the chromosome was replaced by the CJ7 promoter (KCCM10617, Korean Patent NO. 10-0620092) that was newly developed by the present inventors.

Putrescine productivities of 6 types of NCgl2522-enhanced strains thus prepared were compared with that of the parent strain, and as a result, putrescine productivity was increased in all of the strains prepared by additional introduction of NCgl2522 into the transposon, compared to the parent strain (see Table 6). Intracellular putrescine concentrations were measured in the NCgl2522-enhanced strains showing an improvement in putrescine productivity, and as a result, they showed reductions of intracellular putrescine concentrations, compared to the parent strain (see Table 9). Based on these results, the present inventors confirmed that extracellular export of putrescine intracellularly produced is increased by enhancing NCgl2522 activity in the putrescine-producing strains, thereby improving putrescine productivity.

Accordingly, the *Corynebacterium* sp. microorganism having an enhanced putrescine productivity, in which the putrescine-producing strain *Corynebacterium glutamicum* KCCM11138P was modified to have enhanced NCgl2522 activity, compared to the endogenous activity, and thus exhibits an enhanced ability to export putrescine, was designated as *Corynebacterium glutamicum* CC01-0510, and deposited under the Budapest Treaty to the Korean Culture Center of Microorganisms (KCCM) on Mar. 8, 2013, with Accession No. KCCM11401P.

According to another aspect of the present invention, the present invention provides a method for producing putrescine, including the steps of:

(i) culturing the microorganism having putrescine productivity to obtain a cell culture; and (ii) recovering putrescine from the cultured microorganism or the cell culture.

In the method, the step of culturing the microorganism may be, but is not particularly limited to, preferably performed by batch culture, continuous culture, and fed-batch culture known in the art. In this regard, the culture conditions are not particularly limited, but an optimal pH (e.g., pH 5 to 9, preferably pH 6 to 8, and most preferably pH 6.8) can be maintained by using a basic chemical (e.g., sodium hydroxide, potassium hydroxide or ammonia) or acidic chemical (e.g., phosphoric acid or sulfuric acid). Also, an aerobic condition can be maintained by adding oxygen or oxygen-containing gas mixture to a cell culture. The culture temperature may be maintained at 20 to 45° C., and preferably at 25 to 40° C. In addition, the cultivation is preferably performed for about 10 to 160 hours. The putrescine produced by the above cultivation may be excreted to a culture medium or remain inside the cell.

Furthermore, the culture medium to be used may include sugar and carbohydrate (e.g., glucose, sucrose, lactose, fructose, maltose, molasse, starch and cellulose), oil and fat (e.g., soybean oil, sunflower seed oil, peanut oil and coconut oil), fatty acid (e.g., palmitic acid, stearic acid and linoleic acid), alcohol (e.g., glycerol and ethanol), and organic acid (e.g., acetic acid) individually or in combination as a carbon source; nitrogen-containing organic compound (e.g., peptone, yeast extract, meat juice, malt extract, corn solution, soybean meal powder and urea), or inorganic compound (e.g., ammonium sulfate, ammonium chloride, ammonium phosphate, ammonium carbonate, and ammonium nitrate) individually or in combination as a nitrogen source; potassium dihydrogen phosphate, dipotassium phosphate, or sodium-containing salt corresponding thereto individually or in combination as a phosphorus source; other essential growth-stimulating substances including metal salts (e.g., magnesium sulfate or iron sulfate), amino acids, and vitamins.

The method for recovering putrescine that is produced in the culturing step of the present invention can be carried out, for example, using a suitable method known in the art according to batch culture, continuous culture, or fed-batch culture, thereby collecting the desired amino acids from the culture.

Hereinafter, the present invention will be described in more detail with reference to Examples. However, these Examples are for illustrative purposes only, and the invention is not intended to be limited by these Examples.

REFERENCE EXAMPLE 1

Preparation of *Corynebacterium* sp. Microorganism Having Putrescine Productivity In order to prepare a *Corynebacterium* sp. microorganism having putrescine productivity, the biosynthetic pathway of arginine from ornithine was blocked, the biosynthetic pathway of ornithine from glutamate was enhanced, and the foreign ornithine decarboxylase (OCD) was introduced to prepare a microorganism provided with putrescine productivity, as described in Korean Patent Publication NO. 10-2012-0064046.

Specifically, based on the *Corynebacterium glutamicum* ATCC13032, a gene encoding ornithine carbamoyltransferase (ArgF) and a gene encoding NCgl1221 which is a protein involved in glutamate export in the chromosome of the strain were deleted by homologous recombination so as to increase the intracellular content of glutamate which is a precursor of ornithine. Further, a gene encoding ornithine decarboxylase (ODC) derived from the wild-type *E. coli*

W3110 which is involved in the synthesis of putrescine from ornithine was introduced into the chromosome of the strain. Furthermore, the own promoter of argCJBD gene cluster which codes for an enzyme involved in the synthesis of ornithine from glutamate was replaced by an improved promoter CJ7 promoter to prepare a *Corynebacterium glutamicum* strain having putrescine productivity. At this time, argCJBD encodes acetyl gamma glutamyl phosphate reductase (ArgC), acetylglutamate synthase or ornithine acetyltransferase (ArgJ), acetylglutamate kinase (ArgB), acetyl ornithine aminotransferase (ArgD) which are involved in the biosynthetic pathway of ornithine from glutamate. The *Corynebacterium glutamicum* strain having putrescine productivity thus prepared was deposited under the Budapest Treaty to the Korean Culture Center of Microorganisms (KCCM) on Nov. 24, 2010, with Accession No. KCCM11138P. A detailed description concerning the preparation of *Corynebacterium* sp. microorganism having putrescine productivity is given in Korean Patent Publication No. 10-2012-0064046, the disclosure of which is incorporated by reference is in its entirety.

REFERENCE EXAMPLE 2

Preparation of *Corynebacterium* sp. Microorganism Having Putrescine Productivity A gene encoding acetyltransferase NCgl1469 in the *Corynebacterium glutamicum* KCCM11138P prepared in Reference Example 1 was weakened to produce no N-acetyl putrescine, thereby *Corynebacterium glutamicum* strain having improved putrescine productivity was prepared as another *Corynebacterium* sp. microorganism having putrescine productivity.

Specifically, based on the nucleotide sequence of the gene encoding NCgl1469 of *Corynebacterium glutamicum* ATCC13032, a pair of primers of SEQ ID NOs: 1 and 2 for obtaining a homologous recombination fragment of the N-terminal region of NCgl1469 and a pair of primers of SEQ ID NOs: 3 and 4 for obtaining a homologous recombination fragment of the C-terminal region of NCgl1469 were constructed as in the following Table 1.

TABLE 1

| Primer | Sequence (5'-3') |
| --- | --- |
| NCgl1469-del-F1_BamHI (SEQ ID NO: 1) | CGGGATCCAACCTTCAGAACGCGAATAC |
| NCgl1469-del-R1_SalI (SEQ ID NO: 2) | CGCGTCGACTTGGCACTGTGATTACCATC |
| NCgl1469-del-F2_SalI (SEQ ID NO: 3) | CGCGTCGACTTGGGTTATATCCCCTCAGA |
| NCgl1469-del-R2_XbaI (SEQ ID NO: 4) | TGCTCTAGATAGTGAGCCAAGACATGGAA |

PCR was performed using the genomic DNA of *Corynebacterium glutamicum* ATCC13032 as a template and two pairs of primers so as to obtain PCR fragments of the N-terminal and C-terminal regions, respectively. These PCR fragments were electrophoresed to obtain the desired fragments. At this time, PCR reaction was carried out for 30 cycle of denaturation for 30 seconds at 95° C., annealing for 30 seconds at 55° C., and extension for 30 seconds at 72° C. The fragment of the N-terminal region thus obtained was treated with restriction enzymes, BamHI and SalI and the fragment of the C-terminal region thus obtained was treated with restriction enzymes, SalI and XbaI. The fragments thus treated were cloned into a pDZ vector treated with restriction enzymes, BamHI and XbaI, so as to construct a plasmid pDZ-NCgl1469(K/O).

The plasmid pDZ-NCgl1469(K/O) was transformed into *Corynebacterium glutamicum* KCCM11138P by electroporation to obtain a transformant. Then, the transformant was plated and cultured on BHIS plate (37 g/l of Braine heart infusion, 91 g/l of sorbitol, 2% agar) containing kanamycin (25 µg/ml) and X-gal (5-bromo-4-chloro-3-indolin-D-galactoside) for colony formation. From the colonies formed on the plate, blue-colored colonies were selected as the strain introduced with the plasmid pDZ-NCgl1469(K/O).

The selected strain was inoculated in CM medium (10 g/l of glucose, 10 g/l of polypeptone, 5 g/l of yeast extract, 5 g/l of beef extract, 2.5 g/l of NaCl, 2 g/l of urea, pH 6.8) and cultured with shaking at 30° C. for 8 hours. Subsequently, each cell culture was serially diluted from $10^{-4}$ to $10^{-10}$. Then diluted samples were plated and cultured on an X-gal-containing solid medium for colony formation.

From the colonies formed, the white colonies which appear at relatively low frequency were selected to prepare a *Corynebacterium glutamicum* strain having improved putrescine productivity by deletion of the gene encoding NCgl1469. The *Corynebacterium* glutamicum strain having improved putrescine productivity thus prepared was designated as KCCM11138P ΔNCgl1469 and deposited under the Budapest Treaty to the Korean Culture Center of Microorganisms (KCCM) on Dec. 26, 2011, with Accession No. KCCM11240P. A detailed description concerning the preparation of *Corynebacterium* sp. microorganism having putrescine productivity is given in Korean Patent Application No. 10-2012-0003634, the disclosure of which is incorporated by reference is in its entirety.

EXAMPLE 1

Exploration of Putrescine Exporter and Selection of Library Clones with Putrescine Resistance

*Corynebacterium glutamicum* has no putrescine biosynthetic pathways. However, when *Corynebacterium glutamicum* is introduced with external ornithine decarboxylase to have an ability to produce putrescine, it produces and excretes putrescine extracellularly. It is indicated the presence of a transporter protein that functions as a passage of putrescine among numerous membrane proteins of *Corynebacterium* sp. microorganism.

In order to separate and isolate the putrescine exporter from the *Corynebacterium* sp. microorganism, a chromosome library of the wild-type *Corynebacterium glutamicum* ATCC13032 was prepared. Specifically, the chromosome of the *Corynebacterium glutamicum* ATCC13032 was treated with the restriction enzyme Sau3AI for incomplete cleavage. A gene fragment of 3~5 kb was separated, and cloned into a pECCG122 vector treated with BamHI (shuttle vector of *E. coli* and *Corynebacterium*; Korean Patent Publication No. 10-1992-0000933).

The *Corynebacterium* chromosome library thus obtained was transformed into the putrescine-producing strain, *Corynebacterium glutamicum* KCCM11138P according to Reference Example 1, and then strains growing in 0.35 M putrescine-containing minimal medium (containing 10 g of glucose, 0.4 g of MgSO$_4$.7H$_2$O, 4 g of NH$_4$Cl, 1 g of KH$_2$PO$_4$, 1 g of K$_2$HPO$_4$, 2 g of urea, 10 mg of FeSO$_4$.7H$_2$O, 1 mg of MnSO$_4$.5H$_2$O, 5 mg of nicotinamide, 5 mg of thiamine hydrochloride, 0.1 mg of biotin, 1 mM arginine, 25 mg of kanamycin, 0.35 M putrescine, based on 1 l of distilled water, pH 7.0) were selected. From about 5.5×10$^5$ transformants introduced with the *Corynebacterium* chromosome library, 413 colonies were selected, and then each library clone, of which putrescine resistance was also confirmed by secondary examination, was re-introduced into the putrescine-producing strain. Finally, one clone (B19), of which putrescine resistance was confirmed by tertiary examination, was selected. The clone was subjected to nucleotide sequence analysis. As a result, It was found to have NCgl2522 in B19 clone (FIG. 1).

NCgl2522 which was isolated as the putrescine exporter from *Corynebacterium* glutamicum ATCC13032 has the amino acid sequence represented by SEQ ID NO: 21 which is encoded by a polynucleotide having the nucleotide sequence represented by SEQ ID NO: 20.

EXAMPLE 2

Preparation of NCgl2522-deleted Strain and Examination of its Putrescine Productivity <2-1> Preparation of NCgl2522-deleted Strain from ATCC13032-based Putrescine-Producing Strain In order to examine whether the *Corynebacterium glutamicum* ATCC13032-derived NCgl2522 is involved in putrescine export, a vector for deleting the gene encoding NCgl2522 was constructed.

Specifically, based on the nucleotide sequence of the gene encoding NCgl1469 which is represented by SEQ ID NO: 20, a pair of primers of SEQ ID NOs: 5 and 6 for obtaining a homologous recombination fragment of the N-terminal region of NCgl1469 and a pair of primers of SEQ ID NOs: 7 and 8 for obtaining a homologous recombination fragment of the C-terminal region of NCgl1469 were constructed as in the following Table 2.

TABLE 2

| Primer | Sequence (5'-3') |
| --- | --- |
| NCgl2522-del-F1_BamHI (SEQ ID NO: 5) | CGGGATCCCACGCCTGTCTGGTCGC |
| NCgl2522-del-R1_SalI (SEQ ID NO: 6) | ACGCGTCGACGGATCGTAACTGTAAC-GAATGG |
| NCgl2522-del-F2_SalI (SEQ ID NO: 7) | ACGCGTCGACCGCGTGCATCTTT-GGACAC |
| NCgl2522-del-R2_XbaI (SEQ ID NO: 8) | CTAGTCTAGAGAGCTGCAC-CAGGTAGACG |

PCR was performed using the genomic DNA of *Corynebacterium glutamicum* ATCC13032 as a template and two pairs of primers so as to amplify PCR fragments of the N-terminal and C-terminal regions of NCgl2522 gene. These PCR fragments were electrophoresed to obtain the desired fragments. At this time, PCR reaction was carried out for 30 cycle of denaturation for 30 seconds at 95° C., annealing for 30 seconds at 55° C., and extension for 30 seconds at 72° C. The fragment of the N-terminal region thus obtained was treated with restriction enzymes, BamHI and SalI and the fragment of the C-terminal region thus obtained was treated with restriction enzymes, SalI and XbaI. The fragments thus treated were cloned into the pDZ vector treated with restriction enzymes, BamHI and XbaI, so as to construct a plasmid pDZ-1'NCgl2522(K/O).

The plasmid pDZ-1'NCgl2522(K/O) was transformed into *Corynebacterium glutamicum* KCCM11138P and KCCM11240P of Reference Examples 1 and 2 by electroporation, respectively so as to obtain transformants. Then, the transformants were plated and cultured on BHIS plate (37 g/l of Braine heart infusion, 91 g/l of sorbitol, 2% agar) containing kanamycin (25 μg/ml) and X-gal (5-bromo-4-chloro-3-indolin-D-galactoside) for colony formation. From the colonies formed on the plate, blue-colored colonies were selected as the strain introduced with the plasmid pDZ-1'NCgl2522(K/O).

The selected strains were cultured with shaking in CM medium (10 g/l of glucose, 10 g/l of polypeptone, 5 g/l of yeast extract, 5 g/l of beef extract, 2.5 g/l of NaCl, 2 g/l of urea, pH 6.8) at 30° C. for 8 hours. Subsequently, each cell culture was serially diluted from 10$^{-4}$ to 10$^{-10}$. Then, the diluted samples were plated and cultured on an X-gal-containing solid medium for colony formation. From the colonies formed, the white colonies which appear at relatively low frequency were selected to finally obtain strains in which the gene encoding NCgl2522 was deleted by secondary crossover. The strains finally selected were subjected to PCR using a pair of primers of SEQ ID NO: 5 and 8 to confirm deletion of the gene encoding NCgl2522. The *Corynebacterium glutamicum* mutant strains were designated as KCCM11138P ΔNCgl2522 and KCCM11240P ΔNCgl2522, respectively.

<2-2> Preparation of NCgl2522-deleted Strain from ATCC13869-based Putrescine-producing Strain NCgl2522-deleted strain was prepared from *Corynebacterium glutamicum* ATCC13869-based putrescine-producing strains, DAB12-a (argF deletion, NCgl1221 deletion, *E. coli* speC introduction, arg operon promoter substitution; see Reference Example 1) and DAB12-b (argF deletion, NCgl1221 deletion, *E. coli* speC introduction, arg operon promoter substitution, NCgl1469 deletion, see Reference Example 2) having the same genotype as KCCM11138P and KCCM11240P which are *Corynebacterium glutamicum* ATCC13032-based putrescine-producing strains.

Specifically, to examine the sequences of the gene encoding *Corynebacterium glutamicum* ATCC13869-derived NCgl2522 and the protein expressed therefrom, PCR was performed using the genomic DNA of *Corynebacterium glutamicum* ATCC13869 as a template and a pair of primers of SEQ ID NOs: 5 and 8. At this time, PCR reaction was carried out for 30 cycle of denaturation for 30 seconds at 95° C., annealing for 30 seconds at 55° C., and extension for 2 minutes at 72° C. The PCR product thus obtained was separated by electrophoresis, and subjected to sequencing. As a result, it was found that the nucleotide sequence of gene encoding *Corynebacterium glutamicum* ATCC13869-derived NCgl2522 is represented by SEQ ID NO: 22, and the amino acid sequence of protein encoded thereby is represented by SEQ ID NO: 23. When the amino acid sequence of *Corynebacterium glutamicum* ATCC13032-derived NCgl2522 was compared to that of the *Corynebacterium glutamicum* ATCC13869-derived NCgl2522, they were found to have 98% sequence homology.

In order to delete the gene encoding *Corynebacterium glutamicum* ATCC13869-derived NCgl2522, in the same manner as in Example <2-1>, PCR was performed using the genomic DNA of *Corynebacterium glutamicum* ATCC13869 as a template and two pairs of primers of Table 2 so as to amplify PCR fragments of the N-terminal and C-terminal regions of NCgl2522 gene, respectively. These PCR fragments were electrophoresed to obtain the desired fragments. At this time, PCR reaction was carried out for 30 cycle of denaturation for 30 seconds at 95° C., annealing for 30 seconds at 55° C., and extension for 30 seconds at 72° C. The fragment of the N-terminal region thus obtained was treated with restriction enzymes, BamHI and SalI and the fragment of the C-terminal region thus obtained was treated with restriction enzymes, SalI and XbaI. The fragments thus treated were cloned into the pDZ vector treated with restriction enzymes, BamHI and XbaI, so as to construct a plasmid pDZ-2'NCgl2522(K/O).

In the same manner as in Example <2-1>, the plasmid pDZ-2'NCgl2522(K/O) was transformed into *Corynebacterium glutamicum* DAB12-a and DAB12-b, respectively. Strains, in which the gene encoding NCgl2522 was deleted, were selected. *Corynebacterium glutamicum* mutant strains thus selected were designated as DAB12-a ΔNCgl2522 and DAB12-b ΔNCgl2522, respectively.

<2-3> Evaluation of Putrescine Productivity of NCgl2522-deleted Strain

In order to confirm the effect of NCgl2522 deletion on putrescine productivity in the putrescine-producing strain, putrescine productivities of the *Corynebacterium glutamicum* mutant strains prepared in Examples <2-1> and <2-2> were compared.

Specifically, 4 types of *Corynebacterium glutamicum* mutants (KCCM11138P ΔNCgl2522, KCCM11240P ΔNCgl2522, DAB12-a ΔNCgl2522, and DAB12-b ΔNCgl2522) and 4 types of parent strains (KCCM11138P, KCCM11240P, DAB12-a, and DAB12-b) were plated on CM plate media (1% glucose, 1% polypeptone, 0.5% yeast extract, 0.5% beef extract, 0.25% NaCl, 0.2% urea, 100 μl of 50% NaOH, 2% agar, pH 6.8, based on 1 L) containing 1 mM arginine, and cultured at 30° C. for 24 hours, respectively. 1 platinum loop of each strain thus cultured was inoculated in 25 ml of titer medium (8% Glucose, 0.25% soybean protein, 0.50% corn steep solids, 4% (NH$_4$)$_2$SO$_4$, 0.1% KH$_2$PO$_4$, 0.05% MgSO$_4$.7H$_2$O, 0.15% urea, 100 g of biotin, 3 mg of thiamine hydrochloride, 3 mg of calcium-pantothenic acid, 3 mg of nicotinamide, 5% CaCO$_3$, based on 1 L), and then cultured with shaking at 30° C. and 200 rpm for 98 hours. 1 mM arginine was added to the media for culturing all strains. The putrescine concentration in each culture was measured, and the results are shown in the following Table 3.

TABLE 3

| Host | Genotype | Putrescine (g/L) |
|---|---|---|
| KCCM11138P | (−) | 9.8 |
|  | ΔNCgl2522 | 3.0 |
| KCCM11240P | (−) | 12.4 |
| (KCCM11138P Δ NCgl1469) | Δ NCgl2522 | 1.5 |
| DAB12-a | (−) | 10.2 |
|  | Δ NCgl2522 | 0.7 |
| DAB12-b | (−) | 13.1 |
| (DAB12-a ΔNCgl1469) | Δ NCgl2522 | 0.3 |

As shown in Table 3, a remarkable reduction in putrescine production was observed in 4 types of the NCgl2522-deleted *Corynebacterium glutamicum* mutant strains.

EXAMPLE 3

Preparation of NCgl2522-enhanced Strain and Examination of its Putrescine Productivity <3-1> Introduction of NCgl2522 into Transposon Gene in ATCC13032 Chromosome In order to confirm high production of putrescine by additional chromosomal insertion of NCgl2522 gene (containing a self promoter region) in *Corynebacterium* sp. microorganism KCCM11138P having putrescine productivity, NCgl2522 was introduced into a transposon gene. A vector for transformation, pDZTn (Korean Patent Publication No. 10-2008-0033054) which allows introduction of the gene into a transposon gene on the chromosome of *Corynebacterium* sp. microorganism was used.

The NCgl2522 gene containing the self promoter was amplified using the chromosome of ATCC13032 strain as a template and a pair of primers of SEQ ID NO: 9 and 10 (see Table 4). At this time, PCR reaction was carried out for 30 cycle of denaturation for 30 seconds at 95° C., annealing for 30 seconds at 55° C., and extension for 30 seconds or 2 minutes at 72° C. Through PCR, a gene fragment having a size of 1.88 kb was obtained. This PCR product was electrophoresed in a 0.8% agarose gel to elute and purify a band of the desired size. pDZTn vector was treated with XhoI, and fusion cloning of the NCgl2522 PCR product of ATCC13032 strain was performed. In-FusionHD Cloning Kit (Clontech) was used in the fusion cloning. The resulting plasmid was designated as pDZTn-1'NCgl2522.

TABLE 4

| Primer | Sequence (5'-3') |
|---|---|
| 1'NCgl2522-F-T (SEQ ID NO: 9) | TGTCGGGCCCACTAGTGGTGCGACTTCAATT-GTGCTCTT |
| NCgl2522-R-T (SEQ ID NO: 10) | GAATGAGTTCCTCGAGCTAGTGCG-CATTATTGGCTCC |

The plasmid pDZTn-1'NCgl2522 was transformed into *Corynebacterium glutamicum* KCCM11138P described in Reference Example 1 by electroporation to obtain transformants. From the transformants, a strain in which NCgl2522 was introduced into the transposon was selected in the same manner as in Example 2.

PCR was performed using genomic DNA of the selected strain and a pair of primers of SEQ ID NOs: 9 and 10 to confirm that NCgl2522 was introduced into the transposon by introduction of plasmid pDZTn-1'NCgl2522. At this time, PCR reaction was carried out for 30 cycle of denaturation for 30 seconds at 94° C., annealing for 30 seconds at 55° C., and extension for 2 minutes at 72° C.

A *Corynebacterium glutamicum* mutant strain thus selected was designated as KCCM11138P Tn: 1'NCgl2522.

<3-2> Preparation of NCgl2522 Promoter substituted Strain from ATCC13032-based Putrescine-Producing Strain In order to enhance NCgl2522 activity in the putrescine-producing strain, a CJ7 promoter (WO 2006/65095) was introduced in front of the NCgl2522 start codon on the chromosome.

First, a homologous recombination fragment containing a CJ7 promoter having the nucleotide sequence represented by SEQ ID NO: 24 and having the original NCgl2522 sequence at the both ends of the promoter was obtained. Specifically, PCR was performed using the genomic DNA of *Corynebacterium glutamicum* ATCC13032 as a template and a pair of primers of SEQ ID NOs: 11 and 12 to obtain the 5'-terminal region of CJ7 promoter. At this time, PCR reaction was carried out for 30 cycle of denaturation for 30 seconds at 94° C., annealing for 30 seconds at 55° C., and extension for 30 seconds at 72° C. Further, PCR was performed using a pair of primers of SEQ ID NOs: 13 and 14 under the same conditions to obtain the CJ7 promoter region. Furthermore, PCR was performed using the genomic DNA of *Corynebacterium glutamicum* ATCC13032 as a template and a pair of primers of SEQ ID NOs: 15 and 16 under the same conditions to obtain the 3'-terminal region of CJ7 promoter. The primers used in promoter substitution are the same as in the following Table 5.

TABLE 5

| Primer | Sequence (5'-3') |
|---|---|
| NCgl2522-L5 (SEQ ID NO: 11) | TGCAGGTCGACTCTAGAGTTCTGCG-TAGCTGTGTGCC |
| NCgl2522-L3 (SEQ ID NO: 12) | GGATCGTAACTGTAACGAATGG |
| CJ7-F (SEQ ID NO: 13) | CGTTACAGTTACGATCCAGAAACATCCCAGCGC-TACTAATA |
| CJ7-R (SEQ ID NO: 14) | AGTGTTTCCTTTCGTTGGGTACG |
| NCgl2522-R5 (SEQ ID NO: 15) | CAACGAAAGGAAACACTATGACTTCAGAAAC-CTTACAGGCG |
| NCgl2522-R3 (SEQ ID NO: 16) | TCGGTACCCGGGGATCCCACAAAAAGCG-TAGCGATCAACG |

Each PCR product thus obtained was fusion-cloned into pDZ vector treated with BamHI and XbaI. In-FusionHD Cloning Kit (Clontech) was used in the fusion cloning. The resulting plasmid was designated as pDZ-P(CJ7)-1'NCgl2522.

The plasmid pDZ-P(CJ7)-1'NCgl2522 thus prepared was transformed into *Corynebacterium glutamicum* KCCM11138P and KCCM11240P according to Reference Examples 1 and 2 by electroporation so as to prepare transformants. The transformants thus prepared were inoculated in CM media and cultured with shaking at 30° C. for 8 hours. Each cell culture obtained therefrom was diluted from $10^{-4}$ to $10^{-10}$, and plated and cultured on BHIS plate containing 25 μg/ml of kanamycin and X-gal for colony formation.

The white colonies appear at relatively low frequency, compared to majority of the colonies having blue color, and were selected to finally obtain a strain in which the NCgl2522 promoter was substituted with the CJ7 promoter by secondary crossover. PCR was performed using the genomic DNA of the selected strain as a template and a pair of primers of SEQ ID NOs: 13 and 16 to confirm that the CJ7 promoter was introduced in front of the NCgl2522 start codon on the chromosome by introduction of the plasmid pDZ-1'CJ7(NCgl2522). At this time, PCR reaction was carried out for 30 cycle of denaturation for 30 seconds at 94° C., annealing for 30 seconds at 55° C., and extension for 1 minute at 72° C.

*Corynebacterium glutamicum* mutant strains thus selected were designated as KCCM11138P P(CJ7)-NCgl2522 and KCCM11240P P(CJ7)-NCgl2522, respectively.

<3-3> Introduction of NCgl2522 Gene into Transposon Gene on ATCC13869 Chromosome In order to confirm high production of putrescine by additional chromosomal insertion of NCgl2522 gene in *Corynebacterium glutamicum* ATCC13869-derived putrescine strain, introduction of NCgl2522 (containing the promoter region) into a transposon gene was determined NCgl2522 gene was amplified using the chromosome of ATCC13869 strain as a template and a pair of primers of SEQ ID NOs: 17 and 10 (see Table 6). At this time, PCR reaction was carried out for 30 cycle of denaturation for 30 seconds at 94° C., annealing for 30 seconds at 55° C., and extension for 30 seconds or 2 minutes at 72° C. Through PCR, a gene fragment having a size of 1.97 kb was obtained. The NCgl2522 PCR fragment thus prepared was fusion-cloned into pDZTn vector treated with XhoI. In-FusionHD Cloning Kit (Clontech) was used in the fusion cloning. The resulting plasmid was designated as pDZTn-2'NCgl2522.

TABLE 6

| Primer | Sequence (5'-3') |
|---|---|
| 2'NCgl2522-F-T (SEQ ID NO: 17) | TGTCGGGCCCACTAGTCTTCAATTCGAGTT-GCTGCCAC |
| NCgl2522-R-T (SEQ ID NO: 10) | GAATGAGTTCCTCGAGCTAGTGCG-CATTATTGGCTCC |

The plasmid pDZTn-2'NCgl2522 was transformed into *Corynebacterium glutamicum* DAB12-a in the same manner as in Example <3-1> to confirm introduction of NCgl2522 into the transposon.

A *Corynebacterium glutamicum* mutant strain thus selected was designated as DAB12-a Tn:2'NCgl2522.

<3-4> Preparation of NCgl2522 Promoter-substituted Strain from ATCC13869-based Putrescine-Producing Strain In order to introduce the CJ7 promoter in front of the NCgl2522 start codon of *Corynebacterium glutamicum* ATCC13869, PCR was performed using the genomic DNA of *Corynebacterium glutamicum* ATCC13869 as a template and three pairs of primers given in the following Table 7 in the same manner as in Example <3-2>, respectively. Consequently, PCR fragments of the CJ7 promoter region, its N-terminal region and C-terminal region were amplified and then electrophoresed to obtain the desired fragments. At this time, PCR reaction was carried out for 30 cycle of denaturation for 30 seconds at 94° C., annealing for 30 seconds at 55° C., and extension for 30 seconds at 72° C. PCR fragments of the CJ7 promoter region, its N-terminal region and C-terminal region thus obtained were fusion-cloned into pDZ vector treated with BamHI and XbaI. In-FusionHD Cloning Kit (Clontech) was used in the fusion cloning. The resulting plasmid was designated as pDZ-P(CJ7)-2'NCgl2522.

TABLE 7

| Primer | Sequence (5'-3 ') |
|---|---|
| 2'NCgl2522-L5 (SEQ ID NO: 18) | TGCAGGTCGACTCTAGACAATTCGAGTT-GCTGCCACAC |
| NCgl2522-L3 (SEQ ID NO: 12) | GGATCGTAACTGTAACGAATGG |
| CJ7-F (SEQ ID NO: 13) | CGTTACAGTTACGATCCAGAAACATCCCAGCGC-TACTAATA |

TABLE 7-continued

| Primer | Sequence (5'-3') |
|---|---|
| CJ7-R (SEQ ID NO: 14) | AGTGTTTCCTTTCGTTGGGTACG |
| NCgl2522-R5 (SEQ ID NO: 19) | CAACGAAAGGAAACACTATGAT-TTCAGAAACTTTGCAGGCG |
| NCgl2522-R3 (SEQ ID NO: 17) | TCGGTACCCGGGGATCCCACAAAAAGCG-TAGCGATCAACG |

The plasmid pDZ-'P(CJ7)-2'NCgl2522 was transformed into each of *Corynebacterium glutamicum* DAB12-a and DAB12-b in the same manner as in Example <3-2> to select strains, in which the CJ7 promoter was introduced in front of the NCgl2522 start codon. *Corynebacterium glutamicum* mutant strains thus selected were designated as DAB12-a P(CJ7)-NCgl2522 and DAB12-b P(CJ7)-NCgl2522.

<3-5> Evaluation of Putrescine Productivity of NCgl2522-enhanced Strain

In order to confirm the effect of NCgl2522 activity enhancement by promoter substitution on putrescine productivity in the putrescine-producing strain, putrescine productivities of 6 types of *Corynebacterium glutamicum* mutant strains (KCCM11138P Tn: 1'NCgl2522, KCCM11138P P(CJ7)-NCgl2522, KCCM11240P P(CJ7)-NCgl2522, DAB12-a Tn:2'NCgl2522, DAB12-a P(CJ7)-NCgl2522 and DAB12-b P(CJ7)-NCgl2522) prepared in Examples <3-1> to <3-4> and 4 types of parent strains (KCCM11138P, KCCM11240P, DAB12-a and DAB12-b) were compared. Each strain was cultured in the same manner as in Example 2-3, and the putrescine concentration in each culture was measured, and the results are shown in the following Table 8.

TABLE 8

| Host | Genotype | Putrescine (g/L) |
|---|---|---|
| KCCM11138P | (−) | 9.8 |
| | Tn: 1'NCgl2522 | 11.7 |
| | P(CJ7)-NCgl2522 | 13.5 |
| KCCM11240P | (−) | 12.4 |
| | P(CJ7)-NCgl2522 | 15.5 |
| DAB12-a | (−) | 10.2 |
| | Tn: 2'NCgl2522 | 12.3 |
| | P(CJ7)-NCgl2522 | 14.1 |
| DAB12-b | (−) | 13.1 |
| | P(CJ7)-NCgl2522 | 15.9 |

As shown in Table 8, an increase in putrescine production was observed in all 6 types of *Corynebacterium glutamicum* mutant strains in which NCgl2522 activity was enhanced by additional introduction of NCgl2522 into the transposon or by promoter substitution.

EXAMPLE 4

Measurement of Intracellular Putrescine Concentration of NCgl2522-enhanced Strain In order to confirm that intracellular putrescine concentration is reduced by an enhancing ability to export putrescine in the *Corynebacterium glutamicum* mutant strain having enhanced NCgl2522 activity, intracellular putrescine concentrations in *Corynebacterium glutamicum* mutant strain KCCM11138P Tn: 1'NCgl2522 and in parent strain KCCM11138P were measured by extraction using an organic solvent. Intracellular metabolite analysis was carried out in accordance with a method described in the literature (Nakamura J et al., Appl. Environ. Microbiol. 73(14): 4491-4498, 2007).

First, *Corynebacterium glutamicum* mutant strain KCCM11138P Tn:1'NCgl2522 and parent strain KCCM11138P were inoculated in 25 ml of CM liquid media (1% glucose, 1% polypeptone, 0.5% yeast extract, 0.5% beef extract, 0.25% NaCl, 0.2% urea, 100 l of 50% NaOH, pH 6.8, based on 1 L) containing 1 mM arginine, and cultured with shaking at 30° C. and 200 rpm. When cell growth reached exponential phase during cultivation, cells were isolated from the culture media by rapid vacuum filtration (Durapore HV, 0.45 m; Millipore, Billerica, Mass.). The cell-adsorbed filter was washed with 10 ml of cooled water twice, and then dipped in methanol containing 5 M morpholine ethanesulfonic acid and 5 M methionine sulfone for 10 minutes.

The extraction liquid obtained therefrom was mixed well with an equal volume of chloroform and 0.4-fold volume of water, and the aqueous phase was only applied to a spin column to remove protein contaminants. The filtered extraction liquid was analyzed by capillary electrophoresis mass spectrometry, and the results are shown in the following Table 9.

TABLE 9

| Strain | Putrescine (mM) |
|---|---|
| KCCM11138P | 7 |
| KCCM11138P Tn: 1'NCgl2522 | 2 |

As shown in Table 9, a reduction in the intracellular putrescine concentration was observed in *Corynebacterium glutamicum* mutant strain KCCM11138P Tn:1'NCgl2522 having enhanced NCgl2522 activity, compared to parent strain KCCM11138P, It suggests that an improved ability to export putrescine by enhancement of NCgl2522 activity in *Corynebacterium glutamicum* mutant strain KCCM11138P Tn: 1'NCgl2522, leads to effective extracellular export of intracellular putrescine.

EXAMPLE 5

Evaluation of Putrescine Resistance of NCgl2522-deleted or -enhanced Strain

In order to examine the effect of NCgl2522 on putrescine resistance, putrescine resistance of KCCM11240P, KCCM11240P ΔNCgl2522, and KCCM11240P P(CJ7) NCgl2522 strains was evaluated.

Each strain was inoculated in 2 ml of CM liquid containing 1 mM arginine medium and cultured at 30° C. for about 10 hours, followed by dilution in this order of $10^5$, $10^4$, $10^3$, $10^2$ and $10^1$. Each dilution thus prepared was spotted on 0 M or 0.8 M putrescine-containing CMA plate (1% glucose, 1% polypeptone, 0.5% yeast extract, 0.5% beef extract, 0.25% NaCl, 0.2% urea, 1.8% agar, 1 mM arginine, pH 6.8, based on 1 L) and then cultured at 30° C. for 48 hours to compare growth differences between strains.

As a result, the strains showed two different growth patterns. As shown in FIG. 2, the NCgl2522 gene-deleted strain did not grow under the conditions of a high concentration of putrescine, whereas the NCgl2522 gene-enhanced strain grew up under the same conditions. This result shows that the increased cell growth of KCCM11240P P(CJ7)-NCgl2522 under the conditions of a high concentration of putrescine compared to the parent strain is caused by the increased ability to export putrescine due to enhancement of NCgl2522 gene. As a result, introduction and enhancement of NCgl2522 are essential for fermentation of high-concentrations of putrescine.

EXAMPLE 6

Putrescine Fermentation Through Introduction of NCgl2522 into E. coli

In order to confirm whether putrescine production is increased when NCgl2522 of *Corynebacterium glutamicum* ATCC13032 is expressed in the wild-type *E. coli* strain W3110 having a putrescine biosynthetic pathway, a vector expressing speC which is a putrescine synthetic enzyme or a vector expressing NCgl2522 were introduced into W3110.

In order to prepare the speC-expressing vector, W3110 chromosome as a template and a pair of primers of SEQ ID NOs: 34 and 35 were used to amplify a speC gene fragment of about 2.1 kb (see Table 10). This PCR product was electrophoresed in a 0.8% agarose gel, and then a band of the desired size was eluted and purified. pSE280 vector (Invitrogen) containing Trc promoter was treated with NcoI and EcoRI, and then the speC PCR product was fusion-cloned into this vector. In-Fusion® HD Cloning Kit (Clontech) was used in the fusion cloning. The resulting plasmid was designated as pSE280-speC.

In order to prepare the NCgl2522-expressing vector, pSE280 as a template and a pair of primers of SEQ ID NOs: 36 and 37 were used to obtain a Trc promoter fragment, and *Corynebacterium glutamicum* ATCC13032 chromosome as a template and a pair of primers of SEQ ID NOs: 38 and 39 were used to obtain an NCgl2522 fragment. These PCR products were electrophoresed in a 0.8% agarose gel, and then bands of the desired size were eluted and purified. The trc promoter fragment and the NCgl2522 fragment were fusion-cloned into pcc1BAC treated with HindIII. The resulting plasmid was designated as pcc1BAC-P(trc)NCgl2522.

TABLE 10

| Primer | Sequence (5'-3') |
| --- | --- |
| SPEC-F (SEQ ID NO: 34) | CACAGGAAACAGAC-CATGGATGAAATCAATGAATATTGCCGCCA |
| SPEC-R (SEQ ID NO: 35) | GTG-CAGGTGCTGAATTCTTACTTCAACACATAAC-CGTACAAC |
| Ptrc-F (SEQ ID NO: 36) | TGCAGGCATGCAAGCTTCGACATCATAAC-GGTTCTGGC |
| Ptrc-R (SEQ ID NO: 37) | ATTATACGAGCCGGATGATTAATTG |
| NCgl2522-F (SEQ ID NO: 38) | CATCCGGCTCGTATAATATGACTTCAGAAAC-CTTACAGGC |
| NCgl2522-R (SEQ ID NO: 39) | ATAGAATACTCAAGCTTCTAGTGCG-CATTATTGGCTCC |

The plasmids, pSE280-speC or pcc1BAC-P(trc)-NCgl2522, were transformed into W3110. Transformation into *E. coli* was carried out using 2×TSS solution (Epicentre). pSE280-speC-introduced *E. coli* was plated and cultured on an ampicillin (100 μg/ml) containing LB plate (10 g of Tryptone, 5 g of yeast extract, 10 g of Nacl, 2% agar, based on 1 l) for colony formation. pcc1BAC-P(trc)-NCgl2522-introduced *E. coli* was plated and cultured on a chloramphenicol (35 μg/ml)-containing LB plate for colony formation. Putrescine productivities of the strains thus obtained were examined.

Specifically, W3110, W3110 pSE280-speC, and W3110 pcc1BAC-P(trc)-NCgl2522 were inoculated on LB, LA and LC plates, respectively and cultured at 37° C. for 24 hours, and then inoculated in 25 ml of titer medium (2 g of $(NH_4)_2PO_4$, 6.75 g of $KH_2PO_4$, 0.85 g of citric acid, 0.7 g of $MgSO_4.7H_2O$, 0.5% (v/v) trace element, 10 g of glucose, 3 g of AMS, 30 g of $CaCO_3$, based on 1 L) and cultured at 37° C. for 24 hours. A trace metal solution contains 5 M HCl, 10 g of $FeSO_4.7H_2O$, 2.25 g of $ZnSO_4.7H_2O$, 1 g of $CuSO_4.5H_2O$, 0.5 g of $MnSO_4.5H_2O$, 0.23 g of $Na_2B_4O_7.10H_2O$, 2 g of $CaCl_2.2H_2O$, and 0.1 g of $(NH_4)_6Mo_7O_2.4H_2O$ in 1 L.

The putrescine concentration in each culture was measured, and the results are shown in the following Table 11.

TABLE 11

| Host | Plasmid | Putrescine (mg/L) |
| --- | --- | --- |
| W3110 | (−) | 11 |
|  | pSE280-speC | 56 |
|  | pcc1BAC-P(trc)-NCgl2522 | 250 |

As shown in Table 11, high putrescine production was observed in the W3110 pcc1BAC-P(trc)-NCgl2522 strain introduced with NCgl2522, compared to W3110pcc1BACpSE280-speC strain introduced with the putrescine biosynthetic enzyme, speC.

This result demonstrates that NCgl2522 protein also has the ability to export putrescine in *E. coli*.

The present inventors found that additional introduction of NCgl2522 into the transposon of *Corynebacterium* sp. microorganism KCCM11138P having putrescine productivity was performed to enhance NCgl2522 activity of *Corynebacterium glutamicum* strain, and thus putrescine could be produced in a high yield owing to the increased ability to export putrescine, and they designated the strain as *Corynebacterium glutamicum* CC01-0510, and deposited under the Budapest Treaty to the Korean Culture Center of Microorganisms (KCCM) on Mar. 8, 2013, with Accession No. KCCM11401P.

Based on the above description, it should be understood by those skilled in the art that other specific embodiments may be employed in practicing the invention without departing from the technical idea or essential features of the invention. In this regard, the above-described examples are for illustrative purposes only, and the invention is not intended to be limited by these examples. The scope of the present invention should be understood to include all of the modifications or modified form derived from the meaning and scope of the following claims or its equivalent concepts, rather than the above detailed description.

EFFECT OF THE INVENTION

A *Corynebacterium* sp. microorganism having improved putrescine productivity of the present invention is modified to have enhanced NCgl2522 activity of exporting intracellular putrescine, compared to its endogenous activity, resulting in increased extracellular export of putrescine and increased putrescine resistance.

Further, when NCgl2522 was expressed in *E. coli* containing a putrescine synthetic pathway of the present invention, the amount of extracellular putrescine was found to increase. Accordingly, *Corynebacterium glutamicum*-derived NCgl2522 can be applied to a microorganism having putrescine productivity, which can be widely used in the effective production of putrescine.

What is claimed is:

1. A recombinant microorganism having enhanced putrescine productivity,
wherein the recombinant microorganism comprises a modification that enhances expression of a polynucleotide encoding a protein comprising the amino acid sequence of SEQ ID NO: 21 or 23 as compared to the expression in the same microorganism without the modification that enhances expression,
wherein the microorganism further comprises a modification that enhances expression of a polynucleotide encoding an ornithine decarboxylase (ODC) as compared to the expression in the same microorganism without the modification that enhances expression,
wherein the modification that enhances expression is transformation with an expression vector comprising the polynucleotide or replacing the promoter of the polynucleotide with a heterologous promoter.

2. The recombinant microorganism of claim 1, wherein the recombinant microorganism further comprises a modification that reduces expression of a gene encoding an ornithine carbamoyltransferase (ArgF) and a modification reduces expression of a gene encoding a protein involved in glutamate export as compared to the expression in the same microorganism without the modifications that reduces expression,
wherein the modification that reduces expression is inactivation or disruption of the gene.

3. The recombinant microorganism of claim 2, wherein the ornithine carbamoyltransferase (ArgF) comprises the amino acid sequence of SEQ ID NO: 29, the protein involved in glutamate export comprises the amino acid sequence of SEQ ID NO: 30, and the ornithine decarboxylase (ODC) comprises the amino acid sequence of SEQ ID NO: 33.

4. The recombinant microorganism of claim 1, wherein the recombinant microorganism further comprises a modification that enhances expression of a polynucleotide encoding an acetyl-gamma-glutamyl-phosphate reductase (ArgC), a polynucleotide encoding an acetylglutamate synthase or ornithine acetyltransferase (ArgJ), a polynucleotide encoding an acetylglutamate kinase (ArgB), and a polynucleotide encoding an acetylornithine aminotransferase (ArgD), as compared to the expression in the same microorganism without the modification that enhances expression,
wherein the modification that enhances expression is transformation with an expression vector comprising the polynucleotide or replacing the promoter of the polynucleotide with a heterologous promoter.

5. The recombinant microorganism of claim 4, wherein the acetyl-gamma-glutamyl-phosphate reductase (ArgC), acetylglutamate synthase or ornithine acetyltransferase (ArgJ), acetyl glutamate kinase (ArgB), and acetylornithine aminotransferase (ArgD) comprise the amino acid sequences of SEQ ID NOs: 25, 26, 27 and 28, respectively.

6. The recombinant microorganism of claim 1, wherein the recombinant microorganism further comprises a modification that reduces expression of a gene encoding an acetyltransferase as compared to the activity in the same microorganism without the modification that reduces expression,
wherein the modification that reduces expression is inactivation or disruption of the gene.

7. The recombinant microorganism of claim 6, wherein the acetyltransferase comprises the amino acid sequence of SEQ ID NO: 31 or 32.

8. The recombinant microorganism of claim 1, wherein the microorganism is an *Escherichia* sp. or a *Corynebacterium* sp.

9. The recombinant microorganism of claim 8, wherein the microorganism is *E. coli* or *Corynebacterium glutamicum*.

10. A method for producing putrescine, comprising the steps of:
(i) culturing the recombinant microorganism of any one of claims 1 to 9 to obtain a cell culture; and
(ii) recovering putrescine from the cultured recombinant microorganism or the cell culture.

* * * * *

```
                            SEQUENCE LISTING

<160> NUMBER OF SEQ ID NOS: 39

<210> SEQ ID NO 1
<211> LENGTH: 28
<212> TYPE: DNA
<213> ORGANISM: Artificial Sequence
<220> FEATURE:
<223> OTHER INFORMATION: synthesized primer NCgl1469-del-F1_BamHI

<400> SEQUENCE: 1
cgggatccaa ccttcagaac gcgaatac                                      28

<210> SEQ ID NO 2
<211> LENGTH: 29
<212> TYPE: DNA
<213> ORGANISM: Artificial Sequence
<220> FEATURE:
<223> OTHER INFORMATION: synthesized primer NCgl1469-del-R1_SalI

<400> SEQUENCE: 2
cgcgtcgact tggcactgtg attaccatc                                     29

<210> SEQ ID NO 3
<211> LENGTH: 29
<212> TYPE: DNA
<213> ORGANISM: Artificial Sequence
<220> FEATURE:
<223> OTHER INFORMATION: synthesized primer NCgl1469-del-F2_SalI

<400> SEQUENCE: 3
cgcgtcgact tgggttatat cccctcaga                                     29

<210> SEQ ID NO 4
<211> LENGTH: 29
<212> TYPE: DNA
<213> ORGANISM: Artificial Sequence
<220> FEATURE:
<223> OTHER INFORMATION: synthesized primer NCgl1469-del-R2_XbaI

<400> SEQUENCE: 4
tgctctagat agtgagccaa gacatggaa                                     29

<210> SEQ ID NO 5
<211> LENGTH: 25
<212> TYPE: DNA
<213> ORGANISM: Artificial Sequence
<220> FEATURE:
<223> OTHER INFORMATION: synthesized primer NCgl2522-del-F1_BamHI

<400> SEQUENCE: 5
cgggatccca cgcctgtctg gtcgc                                         25

<210> SEQ ID NO 6
<211> LENGTH: 32
<212> TYPE: DNA
<213> ORGANISM: Artificial Sequence
<220> FEATURE:
<223> OTHER INFORMATION: synthesized primer NCgl2522-del-R1_SalI

<400> SEQUENCE: 6
acgcgtcgac ggatcgtaac tgtaacgaat gg                                 32

<210> SEQ ID NO 7
```

<211> LENGTH: 29
<212> TYPE: DNA
<213> ORGANISM: Artificial Sequence
<220> FEATURE:
<223> OTHER INFORMATION: synthesized primer NCgl2522-del-F2_SalI

<400> SEQUENCE: 7
acgcgtcgac cgcgtgcatc tttggacac                              29

<210> SEQ ID NO 8
<211> LENGTH: 29
<212> TYPE: DNA
<213> ORGANISM: Artificial Sequence
<220> FEATURE:
<223> OTHER INFORMATION: synthesized primer NCgl2522-del-R2_XbaI

<400> SEQUENCE: 8
ctagtctaga gagctgcacc aggtagacg                              29

<210> SEQ ID NO 9
<211> LENGTH: 39
<212> TYPE: DNA
<213> ORGANISM: Artificial Sequence
<220> FEATURE:
<223> OTHER INFORMATION: synthesized primer 1'NCgl2522-F

<400> SEQUENCE: 9
tgtcgggccc actagtctta aattccagtt gttgccacg                   39

<210> SEQ ID NO 10
<211> LENGTH: 37
<212> TYPE: DNA
<213> ORGANISM: Artificial Sequence
<220> FEATURE:
<223> OTHER INFORMATION: synthesized primer NCgl2522-R-T

<400> SEQUENCE: 10
gaatgagttc ctcgagctag tgcgcattat tggctcc                     37

<210> SEQ ID NO 11
<211> LENGTH: 37
<212> TYPE: DNA
<213> ORGANISM: Artificial Sequence
<220> FEATURE:
<223> OTHER INFORMATION: synthesized primer NCgl2522-L5

<400> SEQUENCE: 11
tgcaggtcga ctctagagtt ctgcgtagct gtgtgcc                     37

<210> SEQ ID NO 12
<211> LENGTH: 22
<212> TYPE: DNA
<213> ORGANISM: Artificial Sequence
<220> FEATURE:
<223> OTHER INFORMATION: synthesized primer NCgl2522-L3

<400> SEQUENCE: 12
ggatcgtaac tgtaacgaat gg                                     22

<210> SEQ ID NO 13
<211> LENGTH: 41
<212> TYPE: DNA
<213> ORGANISM: Artificial Sequence
<220> FEATURE:
<223> OTHER INFORMATION: synthesized primer CJ7-F

<400> SEQUENCE: 13
cgttacagtt acgatccaga aacatcccag cgctactaat a                                41

<210> SEQ ID NO 14
<211> LENGTH: 23
<212> TYPE: DNA
<213> ORGANISM: Artificial Sequence
<220> FEATURE:
<223> OTHER INFORMATION: synthesized primer CJ7-R

<400> SEQUENCE: 14
agtgtttcct ttcgttgggt acg                                                    23

<210> SEQ ID NO 15
<211> LENGTH: 41
<212> TYPE: DNA
<213> ORGANISM: Artificial Sequence
<220> FEATURE:
<223> OTHER INFORMATION: synthesized primer NCgl2522-R5

<400> SEQUENCE: 15
caacgaaagg aaacactatg acttcagaaa ccttacaggc g                                41

<210> SEQ ID NO 16
<211> LENGTH: 40
<212> TYPE: DNA
<213> ORGANISM: Artificial Sequence
<220> FEATURE:
<223> OTHER INFORMATION: synthesized primer NCgl2522-R3

<400> SEQUENCE: 16
tcggtacccg gggatcccac aaaaagcgta gcgatcaacg                                  40

<210> SEQ ID NO 17
<211> LENGTH: 38
<212> TYPE: DNA
<213> ORGANISM: Artificial Sequence
<220> FEATURE:
<223> OTHER INFORMATION: synthesized primer 2'NCgl2522-F

<400> SEQUENCE: 17
tgtcgggccc actagtcttc aattcgagtt gctgccac                                    38

<210> SEQ ID NO 18
<211> LENGTH: 38
<212> TYPE: DNA
<213> ORGANISM: Artificial Sequence
<220> FEATURE:
<223> OTHER INFORMATION: synthesized primer 2'NCgl2522-L5

<400> SEQUENCE: 18
tgcaggtcga ctctagacaa ttcgagttgc tgccacac                                    38

<210> SEQ ID NO 19
<211> LENGTH: 41
<212> TYPE: DNA
<213> ORGANISM: Artificial Sequence
<220> FEATURE:
<223> OTHER INFORMATION: synthesized primer 2'NCgl2522-R5

<400> SEQUENCE: 19
caacgaaagg aaacactatg atttcagaaa ctttgcaggc g                                41

<210> SEQ ID NO 20
<211> LENGTH: 1485
<212> TYPE: DNA

<213> ORGANISM: Corynebacterium glutamicum ATCC13032

<400> SEQUENCE: 20

```
atgacttcag aaaccttaca ggcgcaagcg cctacgaaaa cccaacgttg ggctttcctc      60
gccgttatca gcgtggtct ctttctgatc ggtgtagaca actcgattct ctacaccgca     120
ctccctctgc tgcgtgaaca gctcgcagcc accgaaaccc aagcgttgtg gatcatcaac     180
gcatatcccc tgctcatggc gggccttctt ttgggtaccg gcactttggg tgacaaaatc     240
ggccaccgcc ggatgttcct catgggcttg agcattttcg gaatcgcttc acttggtgct     300
gcgtttgctc caactgcgtg ggctcttgtt gctgcgagag cttttccttgg catcggtgcg     360
gcaacgatga tgcctgcaac cttggctctg atccgcatta cgtttgagga tgagcgtgag     420
cgcaacactg caattggtat ttggggttcc gtggcaattc ttggcgctgc ggcaggcccg     480
atcattggtg gtgcgctgtt ggaattcttc tggtggggtt cggttttcct cattaacgtt     540
ccggtggctg ttatcgcgtt gatcgctacg cttttttgtgg cgccggccaa tatcgcgaat     600
ccgtctaagc attgggattt cttgtcgtcg ttctatgcgc tgctcacact tgctgggttg     660
atcatcacga tcaaggaatc tgtgaatact gcacgccata tgcctcttct tttgggtgca     720
gtcatcatgt tgatcattgg tgcggtgttg tttagcagtc gtcagaagaa gatcgaggag     780
ccacttctag atctgtcgtt gttccgtaat cgccttttct taggcggtgt ggttgctgcg     840
ggcatggcga tgtttactgt gtccggtttg gaaatgacta cctcgcagcg tttccagttg     900
tctgtgggtt tcactccact tgaggctggt ttgctcatga tcccagctgc attgggtagc     960
ttcccgatgt ctattatcgg tggtgcaaac ctgcatcgtt ggggcttcaa accgctgatc    1020
agtggtggtt ttgctgccac tgccgttggc atcgccctgt gtatttgggg cgcgactcat    1080
actgatggtt tgccgttttt catcgcgggt ctattcttca tgggcgcggg tgctggttcg    1140
gtaatgtctg tgtcttccac tgcgattatc ggttccgcgc cggtgcgtaa gctggcatg    1200
gcgtcgtcga tcgaagaggt ctcttatgag ttcggcacgc tgttgtctgt cgcgattttg    1260
ggtagcttgt tcccattctt ctactcgctg catgccccgg cagaggttgc ggataacttc    1320
tcggcgggtg ttcaccacgc gattgatggc gatgcggcgc gtgcatcttt ggacaccgca    1380
tacattaacg tgttgatcat tgccctagta tgcgcagtag cggctgctct gatcagcagt    1440
tacctttttcc gcggaaatcc gaagggagcc aataatgcgc actag                    1485
```

<210> SEQ ID NO 21
<211> LENGTH: 494
<212> TYPE: PRT
<213> ORGANISM: Corynebacterium glutamicum ATCC 13032

<400> SEQUENCE: 21

```
Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95
```

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 22
<211> LENGTH: 1485

<212> TYPE: DNA
<213> ORGANISM: Corynebacterium glutamicum ATCC 13869

<400> SEQUENCE: 22

```
atgatttcag aaactttgca ggcgcaagcg cctacgaaaa cccaacgttg ggctttcctc      60
gctgttatca gcgtggtct  ctttctgatc ggtgtagaca actcaatcct ctacaccgca     120
ctcccctgc  tgcgtgaaca actcgcagcc actgaaaccc aagcgttgtg gatcatcaac     180
gcatatcccc tgctcatggc gggtcttctt ttgggtaccg gcactttggg tgacaaaatc     240
ggccaccgcc ggatgttcct catgggcttg agcattttcg gaatcgcttc acttggcgct     300
gcgtttgctc caactgcgtg ggctcttgtt gctgcgagag cttttccttgg catcggtgcg     360
gcgacgatga tgcccgcaac cttggctctg atccgcatta cgtttgaaga tgaacgcgaa     420
cggaacaccg cgattggcat ttggggttct gtggcaattc ttggcgcggc ggcaggtccg     480
atcattggtg gtgcgctgtt ggaattcttc tggtgggggtt cggttttcct cattaacgtt     540
ccggtggctg ttatcgcgtt gatcgctacg cttttgtgg  cgccggccaa tatcgcgaat     600
ccgtccaagc actgggattt cttatcctcg ttctatgcat tgcttaccct tgcaggtttg     660
attgtcacca tcaaagaatc ggtaaacact gcacgtcatc tgccactgct tgtaggtgcc     720
atcatcttgc ttatcattgg tgcggtgttg tttagcagtc gtcagaagaa gatcgaggag     780
ccacttctag atctgtcgtt gttccgtaat cgccttttct taggcggtgt ggttgctgcg     840
ggcatggcga tgtttactgt gtccggttg  gaaatgacta cctcgcagcg tttccagttg     900
tctgtgggtt tcactccact tgaggctggt ttgctcatga tcccagctgc attgggtagc     960
ttcccgatgt ctattatcgg tggtgcaaac ttgcatcgtt ggggcttcaa accgctgatc    1020
agtggtggtt tccttgccac ggcagtcggc atcgccctgt gtatttgggg cgcgactcat    1080
actgatggtt tgccgttttt catcgcgggt ctgttcttca tgggcgcggg tgctggttcg    1140
gtaatgtctg tgtcttccac tgcgattatc ggttccgcgc cggtgcgtaa ggctggcatg    1200
gcgtcgtcga tcgaagaggt ctcttatgag ttcggcacgc tgttgtctgt cgcgattttg    1260
ggtagcttgt tcccattctt ctactcgctg catgccccgg cagaggttgc ggataacttc    1320
tcggcgggtg ttcaccacgc gatttatggc gatgcggcg  tgcatctttt ggacaccgca    1380
tacattaacg tgttgatcat tgccctagta tgcgcagtag cggctgctct gatcagcagt    1440
taccttttcc gcggaaatcc gaagggagcc aataatgcgc actag              1485
```

<210> SEQ ID NO 23
<211> LENGTH: 494
<212> TYPE: PRT
<213> ORGANISM: Corynebacterium glutamicum ATCC 13869

<400> SEQUENCE: 23

```
Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
```

```
                    85                  90                  95
Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
                115                 120                 125

Ala Leu Ile Arg Ile Thr Phe Glu Asp Glu Arg Glu Arg Asn Thr Ala
            130                 135                 140

Ile Gly Ile Trp Gly Ser Val Ala Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Val Thr Ile
        210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
        290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
        370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
            405                 410                 415

Val Ala Ile Leu Gly Ser Leu Phe Pro Phe Phe Tyr Ser Leu His Ala
        420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
            485                 490

<210> SEQ ID NO 24
```

<211> LENGTH: 318
<212> TYPE: DNA
<213> ORGANISM: Artificial Sequence
<220> FEATURE:
<223> OTHER INFORMATION: synthesized promoter CJ7

<400> SEQUENCE: 24

```
agaaacatcc cagcgctact aatagggagc gttgaccttc cttccacgga ccggtaatcg     60
gagtgcctaa aaccgcatgc ggcttaggct ccaagatagg ttctgcgcgg ccgggtaatg    120
catcttcttt agcaacaagt tgaggggtag gtgcaaataa gaacgacata gaaatcgtct    180
cctttctgtt tttaatcaac atacaccacc acctaaaaat tccccgacca gcaagttcac    240
agtattcggg cacaatatcg ttgccaaaat attgtttcgg aatatcatgg gatacgtacc    300
caacgaaagg aaacactc                                                  318
```

<210> SEQ ID NO 25
<211> LENGTH: 357
<212> TYPE: PRT
<213> ORGANISM: Corynebacterium glutamicum

<400> SEQUENCE: 25

```
Met Ile Met His Asn Val Tyr Gly Val Thr Met Thr Ile Lys Val Ala
1               5                   10                  15
Ile Ala Gly Ala Ser Gly Tyr Ala Gly Gly Glu Ile Leu Arg Leu Leu
            20                  25                  30
Leu Gly His Pro Ala Tyr Ala Ser Gly Glu Leu Glu Ile Gly Ala Leu
        35                  40                  45
Thr Ala Ala Ser Thr Ala Gly Ser Thr Leu Gly Glu Leu Met Pro His
    50                  55                  60
Ile Pro Gln Leu Ala Asp Arg Val Ile Gln Asp Thr Thr Ala Glu Thr
65                  70                  75                  80
Leu Ala Gly His Asp Val Val Phe Leu Gly Leu Pro His Gly Phe Ser
                85                  90                  95
Ala Glu Ile Ala Leu Gln Leu Gly Pro Asp Val Thr Val Ile Asp Cys
            100                 105                 110
Ala Ala Asp Phe Arg Leu Gln Asn Ala Ala Asp Trp Glu Lys Phe Tyr
        115                 120                 125
Gly Ser Glu His Gln Gly Thr Trp Pro Tyr Gly Ile Pro Glu Met Pro
    130                 135                 140
Gly His Arg Glu Ala Leu Arg Gly Ala Lys Arg Val Ala Val Pro Gly
145                 150                 155                 160
Cys Phe Pro Thr Gly Ala Thr Leu Ala Leu Leu Pro Ala Val Gln Ala
                165                 170                 175
Gly Leu Ile Glu Pro Asp Val Ser Val Val Ser Ile Thr Gly Val Ser
            180                 185                 190
Gly Ala Gly Lys Lys Ala Ser Val Ala Leu Leu Gly Ser Glu Thr Met
        195                 200                 205
Gly Ser Leu Lys Ala Tyr Asn Thr Ser Gly Lys His Arg His Thr Pro
    210                 215                 220
Glu Ile Ala Gln Asn Leu Gly Glu Val Ser Asp Lys Pro Val Lys Val
225                 230                 235                 240
Ser Phe Thr Pro Val Leu Ala Pro Leu Pro Arg Gly Ile Leu Thr Thr
                245                 250                 255
Ala Thr Ala Pro Leu Lys Glu Gly Val Thr Ala Glu Gln Ala Arg Ala
            260                 265                 270
```

```
Val Tyr Glu Glu Phe Tyr Ala Gln Glu Thr Phe Val His Val Leu Pro
            275                 280                 285

Glu Gly Ala Gln Pro Gln Thr Gln Ala Val Leu Gly Ser Asn Met Cys
    290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
                340                 345                 350

Val Gly Val Ala Pro
            355

<210> SEQ ID NO 26
<211> LENGTH: 388
<212> TYPE: PRT
<213> ORGANISM: Corynebacterium glutamicum

<400> SEQUENCE: 26

Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Val Phe Thr Arg Asn
            35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
            115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
            195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
            275                 280                 285
```

```
Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
370                 375                 380

Ala Tyr Ser Ser
385

<210> SEQ ID NO 27
<211> LENGTH: 317
<212> TYPE: PRT
<213> ORGANISM: Corynebacterium glutamicum

<400> SEQUENCE: 27

Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
                20                  25                  30

Val Val Lys Tyr Gly Gly Asn Ala Met Val Asp Asp Leu Lys Ala
            35                  40                  45

Ala Phe Ala Ala Asp Met Val Phe Leu Arg Thr Val Gly Ala Lys Pro
    50                  55                  60

Val Val His Gly Gly Gly Pro Gln Ile Ser Glu Met Leu Asn Arg
65                  70                  75                  80

Val Gly Leu Gln Gly Glu Phe Lys Gly Phe Arg Val Thr Thr Pro
                85                  90                  95

Glu Val Met Asp Ile Val Arg Met Val Leu Phe Gly Gln Val Gly Arg
                100                 105                 110

Asp Leu Val Gly Leu Ile Asn Ser His Gly Pro Tyr Ala Val Gly Thr
            115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ile Gly Ala Glu
    195                 200                 205

Arg Leu Leu Val Leu Thr Asn Val Glu Gly Leu Tyr Thr Asp Trp Pro
210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
```

```
            260                 265                 270
Arg Ile Ala His Ser Val Leu Leu Glu Leu Leu Thr Met Gly Gly Ile
            275                 280                 285

Gly Thr Met Val Leu Pro Asp Val Phe Asp Arg Glu Asn Tyr Pro Glu
            290                 295                 300

Gly Thr Val Phe Arg Lys Asp Asp Lys Asp Gly Glu Leu
305                 310                 315

<210> SEQ ID NO 28
<211> LENGTH: 391
<212> TYPE: PRT
<213> ORGANISM: Corynebacterium glutamicum

<400> SEQUENCE: 28

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45

Ala Leu Gly His Ala His Pro Ala Ile Ile Glu Ala Val Thr Asn Gln
50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
290                 295                 300

Cys Ala Glu Val Ala Arg Lys Gly Glu Leu Phe Lys Glu Leu Leu Ala
305                 310                 315                 320
```

```
Lys Val Asp Gly Val Asp Val Arg Gly Arg Gly Leu Met Leu Gly
            325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
            355                 360                 365

Thr Pro Pro Leu Val Ile Thr Asp Glu Glu Ile Ala Asp Ala Val Lys
370                 375                 380

Ala Ile Ala Glu Thr Ile Ala
385                 390

<210> SEQ ID NO 29
<211> LENGTH: 319
<212> TYPE: PRT
<213> ORGANISM: Corynebacterium glutamicum

<400> SEQUENCE: 29

Met Thr Ser Gln Pro Gln Val Arg His Phe Leu Ala Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
290                 295                 300
```

Ala Gln Lys Ala Leu Leu Val Trp Leu Leu Ala Asn Gln Pro Arg
305                 310                 315

<210> SEQ ID NO 30
<211> LENGTH: 533
<212> TYPE: PRT
<213> ORGANISM: Corynebacterium glutamicum

<400> SEQUENCE: 30

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Ser Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Ser Glu Glu Pro Glu

```
                355                 360                 365
Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Val Ser Thr Pro Ser Met Thr Val Pro Thr Thr
    450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
        530

<210> SEQ ID NO 31
<211> LENGTH: 203
<212> TYPE: PRT
<213> ORGANISM: Corynebacterium glutamicum

<400> SEQUENCE: 31

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190
```

Ala Met Trp Lys Pro Pro Ala Met Pro Thr Val
        195                 200

<210> SEQ ID NO 32
<211> LENGTH: 203
<212> TYPE: PRT
<213> ORGANISM: Corynebacterium glutamicum

<400> SEQUENCE: 32

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Asp Gly Thr Pro Glu Leu
            180                 185                 190

Ala Met Trp Lys Pro Pro Ala Met Pro Thr Val
        195                 200

<210> SEQ ID NO 33
<211> LENGTH: 711
<212> TYPE: PRT
<213> ORGANISM: Escherichia coli

<400> SEQUENCE: 33

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

```
Met Gly Asn Ser Thr Phe Ala Cys Pro Gly His Gln His Gly Ala Phe
            115                 120                 125
Phe Lys Lys His Pro Ala Gly Arg His Phe Tyr Asp Phe Phe Gly Glu
        130                 135                 140
Asn Val Phe Arg Ala Asp Met Cys Asn Ala Asp Val Lys Leu Gly Asp
145                 150                 155                 160
Leu Leu Ile His Glu Gly Ser Ala Lys Asp Ala Gln Lys Phe Ala Ala
                165                 170                 175
Lys Val Phe His Ala Asp Lys Thr Tyr Phe Val Leu Asn Gly Thr Ser
            180                 185                 190
Ala Ala Asn Lys Val Val Thr Asn Ala Leu Leu Thr Arg Gly Asp Leu
        195                 200                 205
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
            260                 265                 270
Arg Pro Tyr Arg Leu Ala Ile Ile Gln Leu Gly Thr Tyr Asp Gly Thr
        275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Gln Ala Gly Phe
            340                 345                 350
Ser Gln Thr Ser Gln Ile His Lys Lys Asp Asn His Ile Arg Gly Gln
        355                 360                 365
Ala Arg Phe Cys Pro His Lys Arg Leu Asn Asn Ala Phe Met Leu His
    370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
            420                 425                 430
Leu Phe Arg Pro Phe Ile Pro Pro Val Val Asp Gly Lys Leu Trp Gln
        435                 440                 445
Asp Tyr Pro Thr Ser Val Leu Ala Ser Asp Arg Arg Phe Phe Ser Phe
    450                 455                 460
Glu Pro Gly Ala Lys Trp His Gly Phe Glu Gly Tyr Ala Ala Asp Gln
465                 470                 475                 480
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
            500                 505                 510
Ala His Tyr Leu Arg Glu Asn Gly Ile Val Pro Glu Lys Cys Asp Leu
        515                 520                 525
Asn Ser Ile Leu Phe Leu Leu Thr Pro Ala Glu Ser His Glu Lys Leu
```

```
Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 34
<211> LENGTH: 44
<212> TYPE: DNA
<213> ORGANISM: Artificial Sequence
<220> FEATURE:
<223> OTHER INFORMATION: Synthesized SPEC-F primer

<400> SEQUENCE: 34
cacaggaaac agaccatgga tgaaatcaat gaatattgcc gcca                    44

<210> SEQ ID NO 35
<211> LENGTH: 42
<212> TYPE: DNA
<213> ORGANISM: Artificial Sequence
<220> FEATURE:
<223> OTHER INFORMATION: Synthesized SPEC-R primer

<400> SEQUENCE: 35
gtgcaggtgc tgaattctta cttcaacaca taaccgtaca ac                      42

<210> SEQ ID NO 36
<211> LENGTH: 38
<212> TYPE: DNA
<213> ORGANISM: Artificial Sequence
<220> FEATURE:
<223> OTHER INFORMATION: Synthesized Ptrc-F primer

<400> SEQUENCE: 36
tgcaggcatg caagcttcga catcataacg gttctggc                           38

<210> SEQ ID NO 37
<211> LENGTH: 25
<212> TYPE: DNA
<213> ORGANISM: Artificial Sequence
<220> FEATURE:
<223> OTHER INFORMATION: Synthesized Ptrc-R primer
```

```
<400> SEQUENCE: 37
attatacgag ccggatgatt aattg                                               25

<210> SEQ ID NO 38
<211> LENGTH: 40
<212> TYPE: DNA
<213> ORGANISM: Artificial Sequence
<220> FEATURE:
<223> OTHER INFORMATION: Synthesized NCgl2522-F primer

<400> SEQUENCE: 38
catccggctc gtataatatg acttcagaaa ccttacaggc                              40

<210> SEQ ID NO 39
<211> LENGTH: 38
<212> TYPE: DNA
<213> ORGANISM: Artificial Sequence
<220> FEATURE:
<223> OTHER INFORMATION: Synthesized NCgl2522-R primer

<400> SEQUENCE: 39
atagaatact caagcttcta gtgcgcatta ttggctcc                                38
```